United States Patent
Okazawa

(10) Patent No.: US 12,319,731 B2
(45) Date of Patent: Jun. 3, 2025

(54) HUMAN MONOCLONAL ANTIBODY BINDING SPECIFICALLY TO HUMAN HMGB1, AND PHARMACEUTICAL COMPOSITION FOR TREATING OR PREVENTING ALZHEIMER'S DISEASE CONTAINING SAID HUMAN MONOCLONAL ANTIBODY

(71) Applicant: INSTUTITE OF SCIENCE TOKYO, Tokyo (JP)

(72) Inventor: Hitoshi Okazawa, Tokyo (JP)

(73) Assignee: INSTITUTE OF SCIENCE TOKYO, Tokyo (JP)

(*) Notice: Subject to any disclaimer, the term of this patent is extended or adjusted under 35 U.S.C. 154(b) by 1027 days.

(21) Appl. No.: 17/276,916

(22) PCT Filed: Sep. 20, 2019

(86) PCT No.: PCT/JP2019/036926
§ 371 (c)(1),
(2) Date: Aug. 26, 2021

(87) PCT Pub. No.: WO2020/059847
PCT Pub. Date: Mar. 26, 2020

(65) Prior Publication Data
US 2023/0038521 A1 Feb. 9, 2023

(30) Foreign Application Priority Data
Sep. 21, 2018 (JP) ................ 2018-176802

(51) Int. Cl.
*A61K 39/395* (2006.01)
*A61P 25/28* (2006.01)
*C07K 16/18* (2006.01)
*C07K 16/24* (2006.01)
*C12N 15/63* (2006.01)
*A61K 39/00* (2006.01)

(52) U.S. Cl.
CPC .......... *C07K 16/24* (2013.01); *A61K 39/3955* (2013.01); *A61P 25/28* (2018.01); *C07K 16/18* (2013.01); *C12N 15/63* (2013.01); *A61K 39/395* (2013.01); *A61K 2039/54* (2013.01); *C07K 2317/24* (2013.01); *C07K 2317/565* (2013.01); *C07K 2317/92* (2013.01)

(58) Field of Classification Search
CPC ... A61K 39/395; A61K 39/3955; C07K 16/18
See application file for complete search history.

(56) References Cited

U.S. PATENT DOCUMENTS

2015/0361164 A1* 12/2015 Takada ................ A61P 13/12
435/254.2

FOREIGN PATENT DOCUMENTS

| JP | 2004107260 A | 4/2004 | |
| JP | 2008-520552 A | 6/2008 | |
| WO | 2008/099913 A1 | 8/2008 | |
| WO | WO-2018030405 A1 * | 2/2018 | ........... A61K 39/395 |

OTHER PUBLICATIONS

Fujita, Kyota et al. "HMGB1, a pathogenic molecule that induces neurite degeneration via TLR4-MARCKS, is a potential therapeutic target for Alzheimer's disease" Scientific Reports, 6:31895, DOI: 10.1038/srep31895, 15 pages.

Tagawa, Kazuhiko et al. "Comprehensive phosphoproteome analysis unravels the core signaling network that initiates the earliest synapse pathology in preclinical Alzheimer's disease brain" Human Molecular Genetics, 2015, vol. 24, No. 2, pp. 540-558.

* cited by examiner

*Primary Examiner* — Xiaozhen Xie

(74) *Attorney, Agent, or Firm* — Edwin S. Flores; Daniel J. Chalker; Chalker Flores, LLP

(57) ABSTRACT

It is an object of the present invention to provide a human monoclonal antibody that has a high inhibitory activity on phosphorylation of Ser46 of human MARCKS and binds specifically to human HMGB1, and a pharmaceutical composition or the like for treating or preventing Alzheimer's disease, containing the antibody as an active component. A human monoclonal antibody that binds specifically to human HMGB1 and contains a heavy-chain CDR1, a heavy-chain CDR2, and a heavy-chain CDR3 consisting of specific amino acid sequences and a light-chain CDR1, a light-chain CDR2, and a light-chain CDR3 consisting of specific amino acid sequences is used. The human monoclonal antibody can also be used as a pharmaceutical composition for treating or preventing Alzheimer's disease.

7 Claims, 8 Drawing Sheets
Specification includes a Sequence Listing.

hIgG1 heavy chain constant region amino acid sequence (p-FUSE-CHIg-hG1)
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 7

Human kappa light chain constant region amino acid sequence (pFUSE2-CLIg-hK)
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

FIG. 8

```
127-H      EVQLLESGGGLVQPGGSLRLSCAASGFTFS---SYAMS--WVRQAPGKGLEWVS---AISGS
129-H      EVQLLESGGGLVQPGGSLRLSCAASGFTFS---SYAMS--WVRQAPGKGLEWVS---DISGS
213-001-H  EVQLVQSGAEVKKPGSSVKVSCKASGGTFS---SYAIS--WVRQAPGQGLEWMG---GIIPI
213-012-H  EVQLVQSGAEVKKPGSSVKVSCKASGGTFS---SYAIS--WVRQAPGQGLEWMG---GIIPI
           ****:**. :  :**.*::** *** ***  ***.* *******:****:.  *

127-H      GGSTYYADSVKG---RFTISRDNSKNTLYLQMNSLRAEDTAVYYCTK---DGYSSSWDYYYY
129-H      GGSTYYADSVKG---RFTISRDNSKNTLYLQMNSLRAEDTAVYYCAR------------
213-001-H  FGRANYAQKFQG---RVTITADESTSTAYMELSSLRSEDTAVYYCAS------------
213-012-H  FGTANYAQKFQG---RVTITADESTSTAYMELSSLRSEDTAVYYCAS------------
           *  :  **:..:*   *.**: *:*.  * *:::.******* *

127-H      YYGMDV---WGQGTTVTVSS
129-H      GYGMDV---WGQGTMVTVSS
213-001-H  -LVTDY---WGQGTLVTVSS
213-012-H  -LVTDY---WGQGTLVTVSS
               *    ***** ****
```

FIG. 9

```
127-L      DIQMTQSPSSLSASVGDRVTITC---RASQSVSSYLA---WYQQKPGKAPKLLIY---EASNL
129-L      DIQMTQSPSSLSASVGDRVTITC---RASQSVTNYLA---WYQQKPGKAPKLLIY---GASIL
213-001-L  DIQMTQSPSSLSASTGDRVTITC---RASQGISSYLA---WYQQKPGKAPKLLIY---AASTL
213-012-L  DIQMTQSPSSLSASTGDRVTITC---RASQGISSYLA---WYQQKPGKAPKLLIY---AASTL
           **************.*******   ****..::.***   ***************   ** *

127-L      QA--GVPSRFSGSGSGTDFTLTINSLQPEDFATYYC---LQHNSNPLT---FGQGTKLEIK
129-L      ET--GVPSRFSGSGSGTDFTLTINSLQPEDFATYYC---LQHNSTPLT---FGQGTKLEIK
213-001-L  QS--GVPSRFSGSGSGTDFTLTISSLQPEDFATYYC---QQANSFPIT---FGQGTRLEIK
213-012-L  QS--GVPSRFSGSGSGTDFTLTISSLQPEDFATYYC---QQANSFPIT---FGQGTRLEIK
           ::  **********************.***********  * ** *:*   *****:****
```

FIG. 10

FIG. 11A
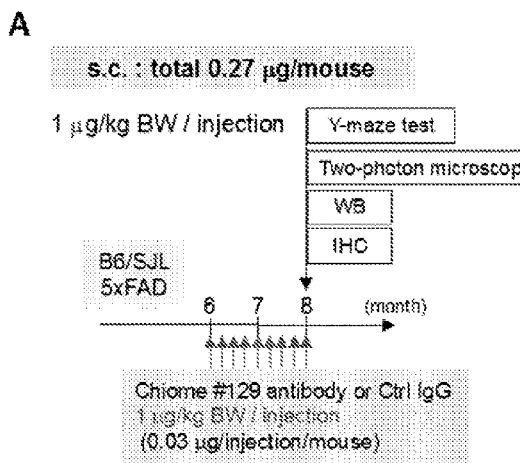
FIG. 11B
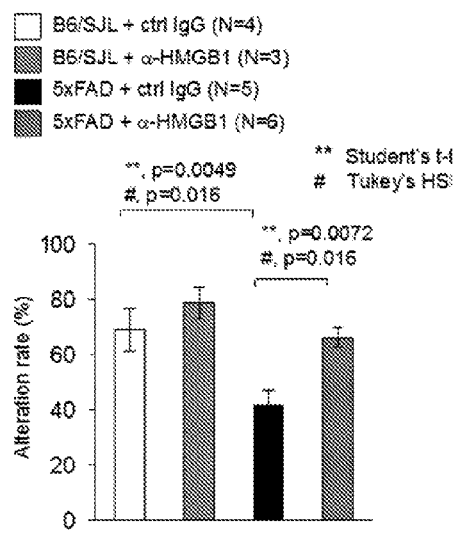
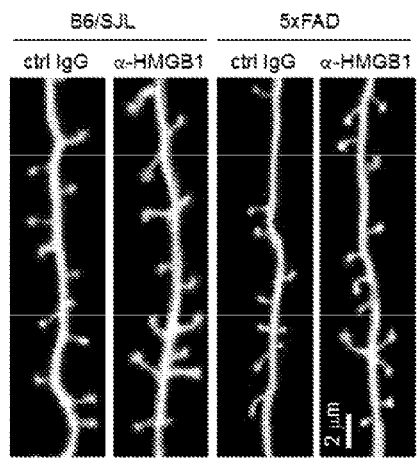
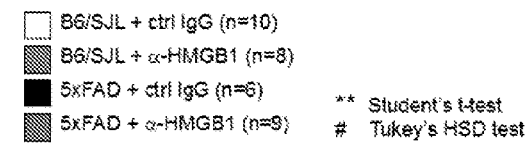
FIG. 11E

SEQUENCE LISTING

```
<160> NUMBER OF SEQ ID NOS: 42

<210> SEQ ID NO 1
<211> LENGTH: 457
<212> TYPE: PRT
<213> ORGANISM: Artificial
```

```
<220> FEATURE:
<223> OTHER INFORMATION: #127 heavy chain (variable region and constant
      region)
<220> FEATURE:
<221> NAME/KEY: MISC_FEATURE
<223> OTHER INFORMATION: Inventor:OKAZAWA, Hitoshi

<400> SEQUENCE: 1
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Thr | Lys | Asp | Gly | Tyr | Ser | Ser | Ser | Trp | Asp | Tyr | Tyr | Tyr | Tyr | Tyr |
| | | | 100 | | | | | 105 | | | | | 110 | |
| Gly | Met | Asp | Val | Trp | Gly | Gln | Gly | Thr | Thr | Val | Thr | Val | Ser | Ser | Ala |
| | | 115 | | | | | 120 | | | | | 125 | | | |
| Ser | Thr | Lys | Gly | Pro | Ser | Val | Phe | Pro | Leu | Ala | Pro | Ser | Ser | Lys | Ser |
| | 130 | | | | | 135 | | | | | 140 | | | | |
| Thr | Ser | Gly | Gly | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser | Gly |
| | | | | 165 | | | | | 170 | | | | | 175 | |
| Val | His | Thr | Phe | Pro | Ala | Val | Leu | Gln | Ser | Ser | Gly | Leu | Tyr | Ser | Leu |
| | | | | 180 | | | | | 185 | | | | | 190 | |
| Ser | Ser | Val | Val | Thr | Val | Pro | Ser | Ser | Ser | Leu | Gly | Thr | Gln | Thr | Tyr |
| | | | 195 | | | | | 200 | | | | | 205 | | |
| Ile | Cys | Asn | Val | Asn | His | Lys | Pro | Ser | Asn | Thr | Lys | Val | Asp | Lys | Lys |
| | 210 | | | | | 215 | | | | | 220 | | | | |
| Val | Glu | Pro | Lys | Ser | Cys | Asp | Lys | Thr | His | Thr | Cys | Pro | Pro | Cys | Pro |
| 225 | | | | | 230 | | | | | 235 | | | | | 240 |
| Ala | Pro | Glu | Leu | Leu | Gly | Gly | Pro | Ser | Val | Phe | Leu | Phe | Pro | Pro | Lys |
| | | | | 245 | | | | | 250 | | | | | 255 | |
| Pro | Lys | Asp | Thr | Leu | Met | Ile | Ser | Arg | Thr | Pro | Glu | Val | Thr | Cys | Val |
| | | | 260 | | | | | 265 | | | | | 270 | | |
| Val | Val | Asp | Val | Ser | His | Glu | Asp | Pro | Glu | Val | Lys | Phe | Asn | Trp | Tyr |
| | | 275 | | | | | 280 | | | | | 285 | | | |
| Val | Asp | Gly | Val | Glu | Val | His | Asn | Ala | Lys | Thr | Lys | Pro | Arg | Glu | Glu |
| | 290 | | | | | 295 | | | | | 300 | | | | |
| Gln | Tyr | Asn | Ser | Thr | Tyr | Arg | Val | Val | Ser | Val | Leu | Thr | Val | Leu | His |
| 305 | | | | | 310 | | | | | 315 | | | | | 320 |
| Gln | Asp | Trp | Leu | Asn | Gly | Lys | Glu | Tyr | Lys | Cys | Lys | Val | Ser | Asn | Lys |
| | | | | 325 | | | | | 330 | | | | | 335 | |
| Ala | Leu | Pro | Ala | Pro | Ile | Glu | Lys | Thr | Ile | Ser | Lys | Ala | Lys | Gly | Gln |
| | | | 340 | | | | | 345 | | | | | 350 | | |
| Pro | Arg | Glu | Pro | Gln | Val | Tyr | Thr | Leu | Pro | Pro | Ser | Arg | Glu | Glu | Met |
| | | | 355 | | | | | 360 | | | | | 365 | | |
| Thr | Lys | Asn | Gln | Val | Ser | Leu | Thr | Cys | Leu | Val | Lys | Gly | Phe | Tyr | Pro |

```
                    370                 375                 380
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 2
<211> LENGTH: 127
<212> TYPE: PRT
<213> ORGANISM: Artificial
<220> FEATURE:
<223> OTHER INFORMATION: #127 heavy chain variable region

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Asp Gly Tyr Ser Ser Ser Trp Asp Tyr Tyr Tyr Tyr Tyr Tyr
            100                 105                 110

Gly Met Asp Val Trp Gly Gln Gly Thr Thr Val Thr Val Ser Ser
        115                 120                 125

<210> SEQ ID NO 3
<211> LENGTH: 5
<212> TYPE: PRT
<213> ORGANISM: Artificial
<220> FEATURE:
<223> OTHER INFORMATION: #127 heavy chain CDR1

<400> SEQUENCE: 3

Ser Tyr Ala Met Ser
1               5

<210> SEQ ID NO 4
<211> LENGTH: 17
<212> TYPE: PRT
<213> ORGANISM: Artificial
<220> FEATURE:
<223> OTHER INFORMATION: #127 heavy chain CDR2

<400> SEQUENCE: 4

Ala Ile Ser Gly Ser Gly Gly Ser Thr Tyr Tyr Ala Asp Ser Val Lys
1               5                   10                  15

Gly
```

```
<210> SEQ ID NO 5
<211> LENGTH: 18
<212> TYPE: PRT
<213> ORGANISM: Artificial
<220> FEATURE:
<223> OTHER INFORMATION: #127 heavy chain CDR3

<400> SEQUENCE: 5

Asp Gly Tyr Ser Ser Trp Asp Tyr Tyr Tyr Tyr Gly Met
1               5                  10                  15

Asp Val

<210> SEQ ID NO 6
<211> LENGTH: 213
<212> TYPE: PRT
<213> ORGANISM: Artificial
<220> FEATURE:
<223> OTHER INFORMATION: #127 light chain (variable region and constant
      region)

<400> SEQUENCE: 6

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gln Gly Thr Lys Leu Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 107
<212> TYPE: PRT
<213> ORGANISM: Artificial
<220> FEATURE:
<223> OTHER INFORMATION: #127 light chain variable region

<400> SEQUENCE: 7

Asp Ile Gln Met Thr Gln Ser Pro Ser Ser Leu Ser Ala Ser Val Gly
```

```
                1               5                   10                  15
Asp Arg Val Thr Ile Thr Cys Arg Ala Ser Gln Ser Val Ser Ser Tyr
                20                  25                  30

Leu Ala Trp Tyr Gln Gln Lys Pro Gly Lys Ala Pro Lys Leu Leu Ile
            35                  40                  45

Tyr Glu Ala Ser Asn Leu Gln Ala Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gln Gly Thr Lys Leu Glu Ile Lys
            100                 105
```

<210> SEQ ID NO 8
<211> LENGTH: 11
<212> TYPE: PRT
<213> ORGANISM: Artificial
<220> FEATURE:
<223> OTHER INFORMATION: #127 light chain CDR1

<400> SEQUENCE: 8

```
Arg Ala Ser Gln Ser Val Ser Ser Tyr Leu Ala
1               5                   10
```

<210> SEQ ID NO 9
<211> LENGTH: 7
<212> TYPE: PRT
<213> ORGANISM: Artificial
<220> FEATURE:
<223> OTHER INFORMATION: #127 light chain CDR2

<400> SEQUENCE: 9

```
Glu Ala Ser Asn Leu Gln Ala
1               5
```

<210> SEQ ID NO 10
<211> LENGTH: 9
<212> TYPE: PRT
<213> ORGANISM: Artificial
<220> FEATURE:
<223> OTHER INFORMATION: #127 light chain CDR3

<400> SEQUENCE: 10

```
Leu Gln His Asn Ser Asn Pro Leu Thr
1               5
```

<210> SEQ ID NO 11
<211> LENGTH: 445
<212> TYPE: PRT
<213> ORGANISM: Artificial
<220> FEATURE:
<223> OTHER INFORMATION: #129 heavy chain (variable region and constant
      region)

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45
```

Ser Asp Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Gly Met Asp Val Trp Gly Gln Gly Thr Met Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 12
<211> LENGTH: 115
<212> TYPE: PRT

```
<213> ORGANISM: Artificial
<220> FEATURE:
<223> OTHER INFORMATION: #129 heavy chain variable region

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Met Asp Val Trp Gly Gln Gly Thr Met Val Thr
            100                 105                 110

Val Ser Ser
        115

<210> SEQ ID NO 13
<211> LENGTH: 5
<212> TYPE: PRT
<213> ORGANISM: Artificial
<220> FEATURE:
<223> OTHER INFORMATION: #129 heavy chain CDR1

<400> SEQUENCE: 13

Ser Tyr Ala Met Ser
1               5

<210> SEQ ID NO 14
<211> LENGTH: 17
<212> TYPE: PRT
<213> ORGANISM: Artificial
<220> FEATURE:
<223> OTHER INFORMATION: #129 heavy chain CDR2

<400> SEQUENCE: 14

Asp Ile Ser Gly Ser Gly Gly Ser Thr Tyr Tyr Ala Asp Ser Val Lys
1               5                   10                  15

Gly

<210> SEQ ID NO 15
<211> LENGTH: 6
<212> TYPE: PRT
<213> ORGANISM: Artificial
<220> FEATURE:
<223> OTHER INFORMATION: #129 heavy chain CDR3

<400> SEQUENCE: 15

Gly Tyr Gly Met Asp Val
1               5

<210> SEQ ID NO 16
<211> LENGTH: 213
<212> TYPE: PRT
<213> ORGANISM: Artificial
<220> FEATURE:
<223> OTHER INFORMATION: #129 light chain (variable region and constant
      region)
```

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Ile Leu Glu Thr Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Thr Pro Leu
                85                  90                  95

Thr Phe Gly Gln Gly Thr Lys Leu Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 17
<211> LENGTH: 107
<212> TYPE: PRT
<213> ORGANISM: Artificial
<220> FEATURE:
<223> OTHER INFORMATION: #129 light chain variable region

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Ile Leu Glu Thr Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln His Asn Ser Thr Pro Leu
                85                  90                  95

Thr Phe Gly Gln Gly Thr Lys Leu Glu Ile Lys
            100                 105

<210> SEQ ID NO 18
<211> LENGTH: 11

```
<212> TYPE: PRT
<213> ORGANISM: Artificial
<220> FEATURE:
<223> OTHER INFORMATION: #129 light chain CDR1

<400> SEQUENCE: 18

Arg Ala Ser Gln Ser Val Thr Asn Tyr Leu Ala
1               5                   10

<210> SEQ ID NO 19
<211> LENGTH: 7
<212> TYPE: PRT
<213> ORGANISM: Artificial
<220> FEATURE:
<223> OTHER INFORMATION: #129 light chain CDR2

<400> SEQUENCE: 19

Gly Ala Ser Ile Leu Glu Thr
1               5

<210> SEQ ID NO 20
<211> LENGTH: 9
<212> TYPE: PRT
<213> ORGANISM: Artificial
<220> FEATURE:
<223> OTHER INFORMATION: #129 light chain CDR3

<400> SEQUENCE: 20

Leu Gln His Asn Ser Thr Pro Leu Thr
1               5

<210> SEQ ID NO 21
<211> LENGTH: 444
<212> TYPE: PRT
<213> ORGANISM: Artificial
<220> FEATURE:
<223> OTHER INFORMATION: #213-001 heavy chain (variable region and
      constant region)

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Val Thr Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175
```

-continued

```
Tyr Ser Leu Ser Ser Val Val Thr Val Pro Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 22
<211> LENGTH: 114
<212> TYPE: PRT
<213> ORGANISM: Artificial
<220> FEATURE:
<223> OTHER INFORMATION: #213-001 heavy chain variable region

<400> SEQUENCE: 22

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Ser Leu Val Thr Asp Tyr Trp Gly Gln Gly Thr Leu Val Thr Val
            100                 105                 110

Ser Ser

<210> SEQ ID NO 23
<211> LENGTH: 5
<212> TYPE: PRT
<213> ORGANISM: Artificial
<220> FEATURE:
<223> OTHER INFORMATION: #213-001 heavy chain CDR1

<400> SEQUENCE: 23

Ser Tyr Ala Ile Ser
1               5

<210> SEQ ID NO 24
<211> LENGTH: 17
<212> TYPE: PRT
<213> ORGANISM: Artificial
<220> FEATURE:
<223> OTHER INFORMATION: #213-001 heavy chain CDR2

<400> SEQUENCE: 24

Gly Ile Ile Pro Ile Phe Gly Arg Ala Asn Tyr Ala Gln Lys Phe Gln
1               5                   10                  15

Gly

<210> SEQ ID NO 25
<211> LENGTH: 5
<212> TYPE: PRT
<213> ORGANISM: Artificial
<220> FEATURE:
<223> OTHER INFORMATION: #213-001 heavy chain CDR3

<400> SEQUENCE: 25

Leu Val Thr Asp Tyr
1               5

<210> SEQ ID NO 26
<211> LENGTH: 213
<212> TYPE: PRT
<213> ORGANISM: Artificial
<220> FEATURE:
<223> OTHER INFORMATION: #213-001 light chain (variable region and
      constant region)

<400> SEQUENCE: 26

Asp Ile Gln Met Thr Gln Ser Pro Ser Ser Leu Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Thr Val Ala Ala Pro
            100                 105                 110

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 27
<211> LENGTH: 107
<212> TYPE: PRT
<213> ORGANISM: Artificial
<220> FEATURE:
<223> OTHER INFORMATION: #213-001 light chain variable region

<400> SEQUENCE: 27

Asp Ile Gln Met Thr Gln Ser Pro Ser Ser Leu Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 28
<211> LENGTH: 11
<212> TYPE: PRT
<213> ORGANISM: Artificial
<220> FEATURE:
<223> OTHER INFORMATION: #213-001 light chain CDR1

<400> SEQUENCE: 28

Arg Ala Ser Gln Gly Ile Ser Ser Tyr Leu Ala
1               5                   10

<210> SEQ ID NO 29
<211> LENGTH: 7
<212> TYPE: PRT
<213> ORGANISM: Artificial
<220> FEATURE:
<223> OTHER INFORMATION: #213-001 light chain CDR2

<400> SEQUENCE: 29

Ala Ala Ser Thr Leu Gln Ser
1               5
```

-continued

```
<210> SEQ ID NO 30
<211> LENGTH: 9
<212> TYPE: PRT
<213> ORGANISM: Artificial
<220> FEATURE:
<223> OTHER INFORMATION: #213-001 light chain CDR3

<400> SEQUENCE: 30

Gln Gln Ala Asn Ser Phe Pro Ile Thr
1               5

<210> SEQ ID NO 31
<211> LENGTH: 444
<212> TYPE: PRT
<213> ORGANISM: Artificial
<220> FEATURE:
<223> OTHER INFORMATION: #213-012 heavy chain (variable region and
      constant region)

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Val Thr Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440
```

```
<210> SEQ ID NO 32
<211> LENGTH: 114
<212> TYPE: PRT
<213> ORGANISM: Artificial
<220> FEATURE:
<223> OTHER INFORMATION: #213-012 heavy chain variable region

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Val Thr Asp Tyr Trp Gly Gln Gly Thr Leu Val Thr Val
            100                 105                 110

Ser Ser
```

```
<210> SEQ ID NO 33
<211> LENGTH: 5
<212> TYPE: PRT
<213> ORGANISM: Artificial
<220> FEATURE:
<223> OTHER INFORMATION: #213-012 heavy chain CDR1

<400> SEQUENCE: 33

Ser Tyr Ala Ile Ser
1               5
```

```
<210> SEQ ID NO 34
<211> LENGTH: 17
<212> TYPE: PRT
<213> ORGANISM: Artificial
```

```
<220> FEATURE:
<223> OTHER INFORMATION: #213-012 heavy chain CDR2

<400> SEQUENCE: 34

Gly Ile Ile Pro Ile Phe Gly Thr Ala Asn Tyr Ala Gln Lys Phe Gln
1               5                   10                  15

Gly

<210> SEQ ID NO 35
<211> LENGTH: 5
<212> TYPE: PRT
<213> ORGANISM: Artificial
<220> FEATURE:
<223> OTHER INFORMATION: #213-012 heavy chain CDR3

<400> SEQUENCE: 35

Leu Val Thr Asp Tyr
1               5

<210> SEQ ID NO 36
<211> LENGTH: 213
<212> TYPE: PRT
<213> ORGANISM: Artificial
<220> FEATURE:
<223> OTHER INFORMATION: #213-012 light chain (variable region and
      constant region)

<400> SEQUENCE: 36

Asp Ile Gln Met Thr Gln Ser Pro Ser Ser Leu Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 37
<211> LENGTH: 107
```

-continued

```
<212> TYPE: PRT
<213> ORGANISM: Artificial
<220> FEATURE:
<223> OTHER INFORMATION: #213-012 light chain variable region

<400> SEQUENCE: 37
```

Asp Ile Gln Met Thr Gln Ser Pro Ser Ser Leu Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

```
<210> SEQ ID NO 38
<211> LENGTH: 11
<212> TYPE: PRT
<213> ORGANISM: Artificial
<220> FEATURE:
<223> OTHER INFORMATION: #213-012 light chain CDR1

<400> SEQUENCE: 38
```

Arg Ala Ser Gln Gly Ile Ser Ser Tyr Leu Ala
1               5                   10

```
<210> SEQ ID NO 39
<211> LENGTH: 7
<212> TYPE: PRT
<213> ORGANISM: Artificial
<220> FEATURE:
<223> OTHER INFORMATION: #213-012 light chain CDR2

<400> SEQUENCE: 39
```

Ala Ala Ser Thr Leu Gln Ser
1               5

```
<210> SEQ ID NO 40
<211> LENGTH: 9
<212> TYPE: PRT
<213> ORGANISM: Artificial
<220> FEATURE:
<223> OTHER INFORMATION: #213-012 light chain CDR3

<400> SEQUENCE: 40
```

Gln Gln Ala Asn Ser Phe Pro Ile Thr
1               5

```
<210> SEQ ID NO 41
<211> LENGTH: 330
<212> TYPE: PRT
<213> ORGANISM: Artificial
<220> FEATURE:
<223> OTHER INFORMATION: the present invention antibody heavy chain
      constant region

<400> SEQUENCE: 41
```

Ala Ser Thr Lys Gly Pro Ser Val Phe Pro Leu Ala Pro Ser Ser Lys

```
                1               5                        10                      15
            Ser Thr Ser Gly Gly Thr Ala Ala Leu Gly Cys Leu Val Lys Asp Tyr
                            20                      25                      30

Phe Pro Glu Pro Val Thr Val Ser Trp Asn Ser Gly Ala Leu Thr Ser
                            35                      40                      45

Gly Val His Thr Phe Pro Ala Val Leu Gln Ser Ser Gly Leu Tyr Ser
                            50                      55                      60

Leu Ser Ser Val Val Thr Val Pro Ser Ser Leu Gly Thr Gln Thr
            65                      70                      75                      80

Tyr Ile Cys Asn Val Asn His Lys Pro Ser Asn Thr Lys Val Asp Lys
                                    85                      90                      95

Lys Val Glu Pro Lys Ser Cys Asp Lys Thr His Thr Cys Pro Pro Cys
                            100                     105                     110

Pro Ala Pro Glu Leu Leu Gly Gly Pro Ser Val Phe Leu Phe Pro Pro
                            115                     120                     125

Lys Pro Lys Asp Thr Leu Met Ile Ser Arg Thr Pro Glu Val Thr Cys
            130                     135                     140

Val Val Val Asp Val Ser His Glu Asp Pro Glu Val Lys Phe Asn Trp
            145                     150                     155                     160

Tyr Val Asp Gly Val Glu Val His Asn Ala Lys Thr Lys Pro Arg Glu
                                    165                     170                     175

Glu Gln Tyr Asn Ser Thr Tyr Arg Val Val Ser Val Leu Thr Val Leu
                            180                     185                     190

His Gln Asp Trp Leu Asn Gly Lys Glu Tyr Lys Cys Lys Val Ser Asn
                            195                     200                     205

Lys Ala Leu Pro Ala Pro Ile Glu Lys Thr Ile Ser Lys Ala Lys Gly
                    210                     215                     220

Gln Pro Arg Glu Pro Gln Val Tyr Thr Leu Pro Pro Ser Arg Glu Glu
            225                     230                     235                     240

Met Thr Lys Asn Gln Val Ser Leu Thr Cys Leu Val Lys Gly Phe Tyr
                                    245                     250                     255

Pro Ser Asp Ile Ala Val Glu Trp Glu Ser Asn Gly Gln Pro Glu Asn
                            260                     265                     270

Asn Tyr Lys Thr Thr Pro Pro Val Leu Asp Ser Asp Gly Ser Phe Phe
                            275                     280                     285

Leu Tyr Ser Lys Leu Thr Val Asp Lys Ser Arg Trp Gln Gln Gly Asn
                    290                     295                     300

Val Phe Ser Cys Ser Val Met His Glu Ala Leu His Asn His Tyr Thr
            305                     310                     315                     320

Gln Lys Ser Leu Ser Leu Ser Pro Gly Lys
                            325                     330

<210> SEQ ID NO 42
<211> LENGTH: 106
<212> TYPE: PRT
<213> ORGANISM: Artificial
<220> FEATURE:
<223> OTHER INFORMATION: the present invention antibody light chain
      constant region (kappa chain)

<400> SEQUENCE: 42

Thr Val Ala Ala Pro Ser Val Phe Ile Phe Pro Pro Ser Asp Glu Gln
            1               5                       10                      15

Leu Lys Ser Gly Thr Ala Ser Val Val Cys Leu Leu Asn Asn Phe Tyr
                            20                      25                      30
```

-continued

```
Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100             105
```

HUMAN MONOCLONAL ANTIBODY BINDING SPECIFICALLY TO HUMAN HMGB1, AND PHARMACEUTICAL COMPOSITION FOR TREATING OR PREVENTING ALZHEIMER'S DISEASE CONTAINING SAID HUMAN MONOCLONAL ANTIBODY

CROSS-REFERENCE TO RELATED APPLICATIONS

This application is the National Stage of International Application No. PCT/JP2019/036926, filed on Sep. 20, 2019 claiming the priority of JP 2018-176802, filed on Sep. 21, 2018, the content of each of which is incorporated by reference herein.

TECHNICAL FIELD

The present invention relates to a human monoclonal antibody that binds specifically to human HMGB1 (that is, anti-human HMGB1 human monoclonal antibody), and a pharmaceutical composition for treating or preventing Alzheimer's disease, comprising the human monoclonal antibody.

BACKGROUND ART

Alzheimer's disease (Alzheimer's type dementia, AD) is a progressive neurodegenerative disease that occurs in the presenile period to the senile period. The main symptoms thereof are memory impairment, cognitive impairment, higher brain dysfunction (such as aphasia, apraxia, agnosia, and constructional apraxia), personality changes, and the like. Due to such symptoms, not only the quality of life of the patient himself/herself is deteriorated, but also the surrounding life of the family and the like are greatly affected. Further, the number of patients is steadily increasing with aging of the population, so that Alzheimer's disease has become a serious problem in the modern society worldwide.

Therefore, Alzheimer's disease is being diligently studied. For example, it has been revealed that Alzheimer's disease is neuropathologically characterized also by deposition of senile plaques and neurofibrillary tangles (such as tangles of neurofibrils and deposition of paired helical filaments (PHF)). Such deposition of these structures is considered to cause nerve dysfunction and nerve cell death (loss of nerve cells) involved in the aforementioned various symptoms.

Further, it has been revealed that senile plaques are structures generated due to polypeptides of about 40 amino acids called amyloid β (Aβ) aggregating and depositing outside the nerve cells at high density. Further, it has been revealed that neurofibrillary tangles are structures generated due to tau proteins, which are microtubule-associated proteins, being phosphorylated, thereby dissociated from the microtubes that form the cytoskeleton, and polymerized to each other.

Thus, the etiology and pathogenic mechanism of Alzheimer's disease is considered to be that Aβ aggregates (amyloid lesions) occur, and the aggregates promote tau phosphorylation and polymerization (tau lesions), leading to the nerve cell death, or the like (amyloid cascade hypothesis). However, the pathogenic mechanism and the like of Alzheimer's disease have not yet been completely clarified, and no eradicative medicine has been provided yet.

Meanwhile, HMGB1 (High Mobility Group Box 1) protein is known as one of the non-histone chromatin-related proteins involved in DNA structure maintenance and transcriptional regulation. In recent years, HMGB1 is gaining attention as not only having such an intranuclear function but also having a function as so-called DAMPs (damage-associated molecular patterns) by being released extracellularly due to cell necrosis or actively secreted extracellularly in response to a vasculitis signal. Further, it has been reported that HMGB1 suppresses phagocytosis by microglia. Thus, it is suggested that HMGB1 is associated with lesions such as Alzheimer's disease since the phagocytosis removes Aβ aggregates (Patent Documents 1 and 2).

Meanwhile, the inventors performed a comprehensive proteome analysis on postmortem brains of Alzheimer's disease model mice and Alzheimer's disease patients and analyzed the abnormal phosphorylation signal network common to Alzheimer's disease. As a result, the inventors have found that phosphorylation of a substrate for a kinase called MARCKS occurs from an early stage before the onset of Alzheimer's disease (Non Patent Document 1). The inventors further have found that phosphorylation of the 46th serine (Ser46) of MARCKS occurs from an early stage before the onset of Alzheimer's disease, and HMGB1 leaked from cells due to neuronal necrosis induces phosphorylation of MARCKS and degeneration of neurites. Then, they produced a mouse monoclonal antibody against HMGB1 and found that such a mouse monoclonal antibody inhibits phosphorylation of Ser46 of MARCKS (Non Patent Document 2). The inventors have confirmed that the mouse monoclonal antibody restores cognitive impairment in Alzheimer's disease model mice, reduces DNA damage in the cerebral cortex, and inhibits multimer formation of both Aβ and HMGB1 (Non Patent Document 2 and Patent Document 3).

PRIOR ART DOCUMENTS

Patent Documents

Patent Document 1: Japanese unexamined Patent Application Publication No. 2004-107260
Patent Document 2: International Publication No. WO 2008/099913
Patent Document 3: International Publication No. WO 2018/030405

Non Patent Documents

Non Patent Document 1: Human Molecular Genetics, 2015 Jan. 15; 24 (2): 540-58
Non Patent Document 2: SCIENTIFIC REPORT, 2016 Aug. 25; 6: 31895

SUMMARY OF THE INVENTION

Object to be Solved by the Invention

It is an object of the present invention to provide a human monoclonal antibody that has a high inhibitory activity on phosphorylation of Ser46 of human MARCKS and binds specifically to human HMGB1, and a pharmaceutical composition or the like for treating or preventing Alzheimer's disease, comprising the antibody as an active component.

Means to Solve the Object

Under the aforementioned circumstances of the background art as described above, the inventors have conducted dedicated studies in order to obtain a human monoclonal antibody which is expected to have preventive or therapeutic effects on Alzheimer's disease in humans superior to the mouse monoclonal antibody of Patent Document 3. Specifically, the inventors have produced 9 kinds of human monoclonal antibodies that bind specifically to human HMGB1, examined the activity of each human monoclonal antibody to inhibit phosphorylation of Ser46 of human MARCKS, found 4 kinds of human monoclonal antibodies having particularly high phosphorylation inhibitory activity, and determined the amino acid sequences and the like of the light-chain variable regions and the heavy-chain variable regions, and the complementarity determining regions (CDR) 1 to 3 of the human monoclonal antibody. Further, the inventors have found that the cognitive dysfunction is suppressed and improved by subcutaneous administration or intravenous injection of the aforementioned human monoclonal antibody to Alzheimer's disease model mice, thereby accomplishing the present invention.

That is, the present invention relates to the following aspects.

(1) A human monoclonal antibody that binds specifically to human HMGB1 and has any one of characteristics (A) to (D) below:
(A) comprising a heavy-chain complementarity determining region (CDR) 1 consisting of the amino acid sequence set forth in SEQ ID NO: 3 or the amino acid sequence with one or more amino acids substituted, deleted, added, and/or inserted, a heavy-chain CDR2 consisting of the amino acid sequence set forth in SEQ ID NO: 4 or the amino acid sequence with one or more amino acids substituted, deleted, added, and/or inserted, and a heavy-chain CDR3 consisting of the amino acid sequence set forth in SEQ ID NO: 5 or the amino acid sequence with one or more amino acids substituted, deleted, added, and/or inserted, and
a light-chain CDR1 consisting of the amino acid sequence set forth in SEQ ID NO: 8 or the amino acid sequence with one or more amino acids substituted, deleted, added, and/or inserted, a light-chain CDR2 consisting of the amino acid sequence set forth in SEQ ID NO: 9 or the amino acid sequence with one or more amino acids substituted, deleted, added, and/or inserted, and a light-chain CDR3 consisting of the amino acid sequence set forth in SEQ ID NO: 10 or the amino acid sequence with one or more amino acids substituted, deleted, added, and/or inserted;
(B) comprising a heavy-chain complementarity determining region (CDR) 1 consisting of the amino acid sequence set forth in SEQ ID NO: 13 or the amino acid sequence with one or more amino acids substituted, deleted, added, and/or inserted, a heavy-chain CDR2 consisting of the amino acid sequence set forth in SEQ ID NO: 14 or the amino acid sequence with one or more amino acids substituted, deleted, added, and/or inserted, and a heavy-chain CDR3 consisting of the amino acid sequence set forth in SEQ ID NO: 15 or the amino acid sequence with one or more amino acids substituted, deleted, added, and/or inserted, and
a light-chain CDR1 consisting of the amino acid sequence set forth in SEQ ID NO: 18 or the amino acid sequence with one or more amino acids substituted, deleted, added, and/or inserted, a light-chain CDR2 consisting of the amino acid sequence set forth in SEQ ID NO: 19 or the amino acid sequence with one or more amino acids substituted, deleted, added, and/or inserted, and a light-chain CDR3 consisting of the amino acid sequence set forth in SEQ ID NO: 20 or the amino acid sequence with one or more amino acids substituted, deleted, added, and/or inserted;
(C) comprising a heavy-chain complementarity determining region (CDR) 1 consisting of the amino acid sequence set forth in SEQ ID NO: 23 or the amino acid sequence with one or more amino acids substituted, deleted, added, and/or inserted, a heavy-chain CDR2 consisting of the amino acid sequence set forth in SEQ ID NO: 24 or the amino acid sequence with one or more amino acids substituted, deleted, added, and/or inserted, and a heavy-chain CDR3 consisting of the amino acid sequence set forth in SEQ ID NO: 25 or the amino acid sequence with one or more amino acids substituted, deleted, added, and/or inserted, and
a light-chain CDR1 consisting of the amino acid sequence set forth in SEQ ID NO: 28 or the amino acid sequence with one or more amino acids substituted, deleted, added, and/or inserted, a light-chain CDR2 consisting of the amino acid sequence set forth in SEQ ID NO: 29 or the amino acid sequence with one or more amino acids substituted, deleted, added, and/or inserted, and a light-chain CDR3 consisting of the amino acid sequence set forth in SEQ ID NO: 30 or the amino acid sequence with one or more amino acids substituted, deleted, added, and/or inserted; and
(D) comprising a heavy-chain complementarity determining region (CDR) 1 consisting of the amino acid sequence set forth in SEQ ID NO: 33 or the amino acid sequence with one or more amino acids substituted, deleted, added, and/or inserted, a heavy-chain CDR2 consisting of the amino acid sequence set forth in SEQ ID NO: 34 or the amino acid sequence with one or more amino acids substituted, deleted, added, and/or inserted, and a heavy-chain CDR3 consisting of the amino acid sequence set forth in SEQ ID NO: 35 or the amino acid sequence with one or more amino acids substituted, deleted, added, and/or inserted, and
a light-chain CDR1 consisting of the amino acid sequence set forth in SEQ ID NO: 38 or the amino acid sequence with one or more amino acids substituted, deleted, added, and/or inserted, a light-chain CDR2 consisting of the amino acid sequence set forth in SEQ ID NO: 39 or the amino acid sequence with one or more amino acids substituted, deleted, added, and/or inserted, and a light-chain CDR3 consisting of the amino acid sequence set forth in SEQ ID NO: 40 or the amino acid sequence with one or more amino acids substituted, deleted, added, and/or inserted.
(2) The human monoclonal antibody according to (1) above, wherein the human monoclonal antibody having characteristic (A) further has characteristic (a) below, the human monoclonal antibody having characteristic (B) further has characteristic (b) below, the human monoclonal antibody having characteristic (C) further has characteristic (c) below, and the human monoclonal antibody having characteristic (D) further has characteristic (d) below:
(a) comprising a heavy-chain variable region consisting of an amino acid sequence having a sequence identity of at least 80% with the amino acid sequence set forth in SEQ ID NO: 2 and a light-chain variable region consisting of an amino acid sequence having a sequence identity of at least 80% with the amino acid sequence set forth in SEQ ID NO: 7;
(b) comprising a heavy-chain variable region consisting of an amino acid sequence having a sequence identity of at least 80% with the amino acid sequence set forth in SEQ ID NO: 12 and a light-chain variable region consisting of an amino acid sequence having a sequence identity of at least 80% with the amino acid sequence set forth in SEQ ID NO: 17;

(c) comprising a heavy-chain variable region consisting of an amino acid sequence having a sequence identity of at least 80% with the amino acid sequence set forth in SEQ ID NO: 22 and a light-chain variable region consisting of an amino acid sequence having a sequence identity of at least 80% with the amino acid sequence set forth in SEQ ID NO: 27; and (d) comprising a heavy-chain variable region consisting of an amino acid sequence having a sequence identity of at least 80% with the amino acid sequence set forth in SEQ ID NO: 32 and a light-chain variable region consisting of an amino acid sequence having a sequence identity of at least 80% with the amino acid sequence set forth in SEQ ID NO: 37.

(3) The human monoclonal antibody according to (2) above, wherein the human monoclonal antibody having characteristics (A) and (a) further has characteristic (a1) below, the human monoclonal antibody having characteristics (B) and (b) further has characteristic (b1) below, the human monoclonal antibody having characteristics (C) and (c) further has characteristic (c1) below, and the human monoclonal antibody having characteristics (D) and (d) further has characteristic (d1) below:

(a1) comprising a heavy chain consisting of an amino acid sequence having a sequence identity of at least 80% with the amino acid sequence set forth in SEQ ID NO: 1 and a light chain consisting of an amino acid sequence having a sequence identity of at least 80% with the amino acid sequence set forth in SEQ ID NO: 6;

(b1) comprising a heavy chain consisting of an amino acid sequence having a sequence identity of at least 80% with the amino acid sequence set forth in SEQ ID NO: 11 and a light chain consisting of an amino acid sequence having a sequence identity of at least 80% with the amino acid sequence set forth in SEQ ID NO: 16;

(c1) comprising a heavy chain consisting of an amino acid sequence having a sequence identity of at least 80% with the amino acid sequence set forth in SEQ ID NO: 21 and a light chain consisting of an amino acid sequence having a sequence identity of at least 80% with the amino acid sequence set forth in SEQ ID NO: 26; and (d1) comprising a heavy chain consisting of an amino acid sequence having a sequence identity of at least 80% with the amino acid sequence set forth in SEQ ID NO: 31 and a light chain consisting of an amino acid sequence having a sequence identity of at least 80% with the amino acid sequence set forth in SEQ ID NO: 36.

(4) A composition comprising the human monoclonal antibody according to any one of (1) to (3) above.

(5) A pharmaceutical composition for treating or preventing Alzheimer's disease, comprising the human monoclonal antibody according to any one of (1) to (3) above as an active component.

(6) An antibody gene encoding the human monoclonal antibody according to any one of (1) to (3) above.

(7) A vector comprising: a promoter; and the antibody gene according to (6) above operably linked downstream of the promoter.

(8) A host cell comprising the vector according to (7) above introduced thereinto.

Effect of the Invention

The present invention can provide a human monoclonal antibody that has a high inhibitory activity on phosphorylation of Ser46 of human MARCKS and binds specifically to human HMGB1, and a pharmaceutical composition or the like for treating or preventing Alzheimer's disease, comprising the antibody as an active component.

BRIEF DESCRIPTION OF DRAWINGS

FIG. 7 shows the amino acid sequence (SEQ ID NO: 41) of the heavy-chain constant region of the human monoclonal antibodies of the present invention. The amino acid sequence of the heavy-chain constant region is common to the human monoclonal antibodies of the present invention (monoclonal antibodies #127, #129, #194, #459, #130-008, #213-001, #213-012, #283-010, and #370-010).

FIG. 8 shows the amino acid sequence (SEQ ID NO: 42) of the light-chain constant region (κ chain) of the human monoclonal antibodies of the present invention. The amino acid sequence of the light-chain constant region is common to the human monoclonal antibodies of the present invention (monoclonal antibodies #127, #129, #194, #459, #130-008, #213-001, #213-012, #283-010, and #370-010).

FIG. 9 shows the alignment of the amino acid sequences of the heavy-chain variable regions of the human monoclonal antibodies of the present invention (monoclonal antibodies #127, #129, #213-001, and #213-012) (the amino acid sequences of SEQ ID NOs: 2, 12, 22, and 32, respectively).

FIG. 10 shows the alignment of the amino acid sequences of the light-chain variable regions of the human monoclonal antibodies of the present invention (monoclonal antibodies #127, #129, #213-001, and #213-012) (the amino acid sequences of SEQ ID NOs:7, 17, 27, and 37, respectively).

FIG. 11 shows the effects of subcutaneous administration of a human monoclonal antibody of the present invention (monoclonal antibody #129) on the cognitive function and the dendritic spine density of Alzheimer's disease model mice. FIG. 11A shows the outline of the schedule of antibody administration to mice, and FIG. 11B shows the results of quantifying the cognitive function in each administration group by the Y-maze test. Further, the images on the left of FIG. 11E show synapses (dendritic spines) after imaging with a two-photon excitation microscope, and the graph on the right of FIG. 11E shows the number of spines per 10 μm of dendrites in each administration group. In the figure, "B6/SJL" represents B6/SJL non-transgenic mice (normal mice), and "5xFAD" represents 5xFAD transgenic mice. In the figure, "B6/SJL+ctrl IgG" represents normal mice to which control human IgG was administered, "B6/SJL+α-HMGB1" represents normal mice to which monoclonal antibody #129 was administered, "5xFAD+ctrl IgG" represents Alzheimer's disease model mice to which control human IgG was administered, and "5xFAD+α-HMGB1" represents Alzheimer's disease model mice to which monoclonal antibody #129 was administered. The bar graphs of FIG. 11B and FIG. 11E each show the results of "B6/SJL+ctrl IgG", "B6/SJL+α-HMGB1", "5xFAD+ctrl IgG", and "5xFAD+α-HMGB1" from the left.

FIG. 12 shows the effects of subcutaneous administration or intravenous injection of a human monoclonal antibody of the present invention (monoclonal antibody #129) on the cognitive function of Alzheimer's disease model mice.

MODE OF CARRYING OUT THE INVENTION

Figure 1:
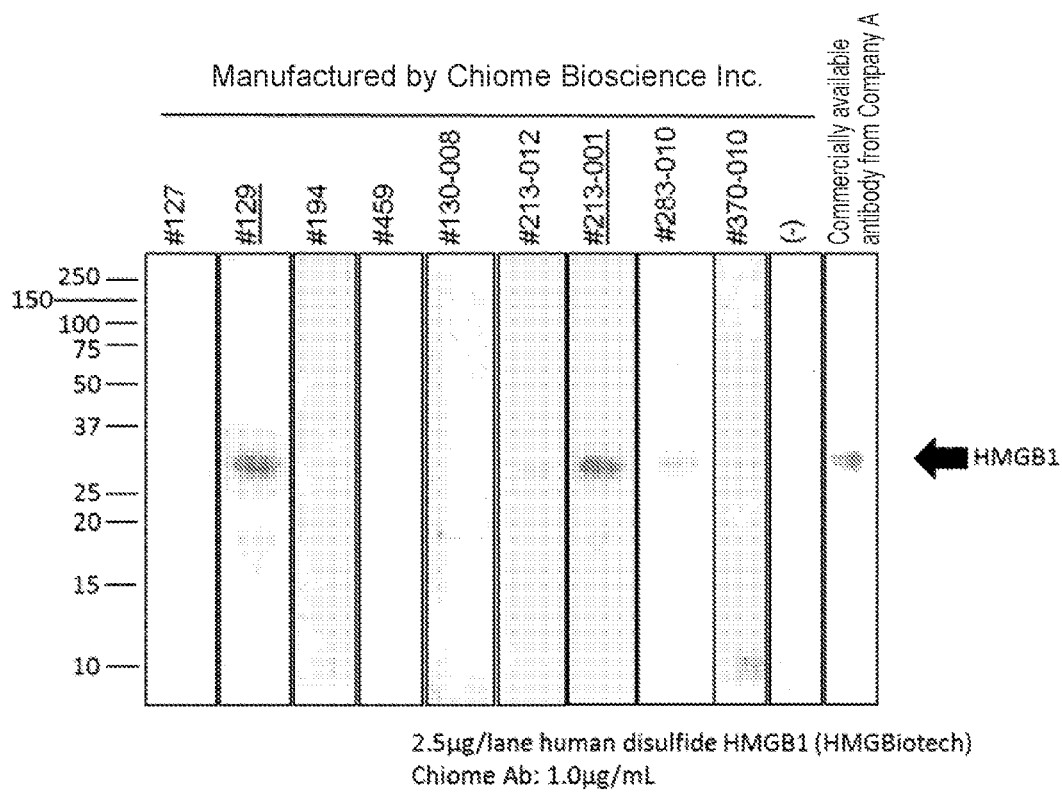
FIG. 1 shows the results of detecting human HMGB1 protein using the human monoclonal antibodies of the present invention by Western blotting. In the figure, "#127", "#129", "#194", "#459", "#130-008", "#213-012", "#213-001", "#283-010", and "#370-010" indicate the results using the human monoclonal antibodies of the present invention as primary antibodies, "(−)" indicates the result with no primary antibody added (negative control), and "commercially available antibody from Company A" indicates the result using a commercially available anti-human HMGB1 antibody as a primary antibody (positive control). In the figure, "HMGB1" represents a human HMGB1 protein signal (band).

The present invention includes the following embodiments, for example.

[1] A human monoclonal antibody that binds specifically to human HMGB1 and has any one of characteristics (A) to (D) below (which will be hereinafter also called "human monoclonal antibody of the present invention");

(A) comprising a heavy-chain complementarity determining region (CDR) 1 consisting of the amino acid sequence set forth in SEQ ID NO: 3 or the amino acid sequence with one or more amino acids substituted, deleted, added, and/or inserted, a heavy-chain CDR2 consisting of the amino acid sequence set forth in SEQ ID NO: 4 or the amino acid sequence with one or more amino acids substituted, deleted, added, and/or inserted, and a heavy-chain CDR3 consisting of the amino acid sequence set forth in SEQ ID NO: 5 or the amino acid sequence with one or more amino acids substituted, deleted, added, and/or inserted, and a light-chain CDR1 consisting of the amino acid sequence set forth in SEQ ID NO: 8 or the amino acid sequence with one or more amino acids substituted, deleted, added, and/or inserted, a light-chain CDR2 consisting of the amino acid sequence set forth in SEQ ID NO: 9 or the amino acid sequence with one or more amino acids substituted, deleted, added, and/or inserted, and a light-chain CDR3 consisting of the amino acid sequence set forth in SEQ ID NO: 10 or the amino acid sequence with one or more amino acids substituted, deleted, added, and/or inserted;

(B) comprising a heavy-chain complementarity determining region (CDR) 1 consisting of the amino acid sequence set forth in SEQ ID NO: 13 or the amino acid sequence with one or more amino acids substituted, deleted, added, and/or inserted, a heavy-chain CDR2 consisting of the amino acid sequence set forth in SEQ ID NO: 14 or the amino acid sequence with one or more amino acids substituted, deleted, added, and/or inserted, and a heavy-chain CDR3 consisting of the amino acid sequence set forth in SEQ ID NO: 15 or the amino acid sequence with one or more amino acids substituted, deleted, added, and/or inserted, and a light-chain CDR1 consisting of the amino acid sequence set forth in SEQ ID NO: 18 or the amino acid sequence with one or more amino acids substituted, deleted, added, and/or inserted, a light-chain CDR2 consisting of the amino acid sequence set forth in SEQ ID NO: 19 or the amino acid sequence with one or more amino acids substituted, deleted, added, and/or inserted, and a light-chain CDR3 consisting of the amino acid sequence set forth in SEQ ID NO: 20 or the amino acid sequence with one or more amino acids substituted, deleted, added, and/or inserted;

(C) comprising a heavy-chain complementarity determining region (CDR) 1 consisting of the amino acid sequence set forth in SEQ ID NO: 23 or the amino acid sequence with one or more amino acids substituted, deleted, added, and/or inserted, a heavy-chain CDR2 consisting of the amino acid sequence set forth in SEQ ID NO: 24 or the amino acid sequence with one or more amino acids substituted, deleted, added, and/or inserted, and a heavy-chain CDR3 consisting of the amino acid sequence set forth in SEQ ID NO: 25 or the amino acid sequence with one or more amino acids substituted, deleted, added, and/or inserted, and a light-chain CDR1 consisting of the amino acid sequence set forth in SEQ ID NO: 28 or the amino acid sequence with one or more amino acids substituted, deleted, added, and/or inserted, a light-chain CDR2 consisting of the amino acid sequence set forth in SEQ ID NO: 29 or the amino acid sequence with one or more amino acids substituted, deleted, added, and/or inserted, and a light-chain CDR3 consisting of the amino acid sequence set forth in SEQ ID NO: 30 or the amino acid sequence with one or more amino acids substituted, deleted, added, and/or inserted; and (D) comprising a heavy-chain complementarity determining region (CDR) 1 consisting of the amino acid sequence set forth in SEQ ID NO: 33 or the amino acid sequence with one or more amino acids substituted, deleted, added, and/or inserted, a heavy-chain CDR2 consisting of the amino acid sequence set forth in SEQ ID NO: 34 or the amino acid sequence with one or more amino acids substituted, deleted, added, and/or inserted, and a heavy-chain CDR3 consisting of the amino acid sequence set forth in SEQ ID NO: 35 or the amino acid sequence with one or more amino acids substituted, deleted, added, and/or inserted, and a light-chain CDR1 consisting of the amino acid sequence set forth in SEQ ID NO: 38 or the amino acid sequence with one or more amino acids substituted, deleted, added, and/or inserted, a light-chain CDR2 consisting of the amino acid sequence set forth in SEQ ID NO: 39 or the amino acid sequence with one or more amino acids substituted, deleted, added, and/or inserted, and a light-chain CDR3 consisting of the amino acid sequence set forth in SEQ ID NO: 40 or the amino acid sequence with one or more amino acids substituted, deleted, added, and/or inserted.

[2] A composition comprising the human monoclonal antibody of the present invention (which will be hereinafter also called "composition of the present invention").

[3] A pharmaceutical composition for treating or preventing Alzheimer's disease, comprising the human monoclonal antibody of the present invention as an active component (which will be hereinafter also called "pharmaceutical composition of the present invention").

[4] An antibody gene encoding the human monoclonal antibody of the present invention (which will be hereinafter also called "antibody gene of the present invention").

[5] A vector comprising: a promoter; and the antibody gene of the present invention operably linked downstream of the promoter (which will be hereinafter also called "the vector of the present invention").

[6] A host cell comprising the vector of the present invention introduced thereto (which will be hereinafter also called "host cell of the present invention").

<Human Monoclonal Antibody of Present Invention>

The human monoclonal antibody of the present invention is not specifically limited as long as it is a human monoclonal antibody that binds specifically to human HMGB1 and has any one of characteristics (A) to (D) below:

(A) comprising a heavy-chain complementarity determining region (CDR) 1 consisting of the amino acid sequence set forth in SEQ ID NO: 3 or the amino acid sequence with one or more amino acids substituted, deleted, added, and/or inserted, a heavy-chain CDR2 consisting of the amino acid sequence set forth in SEQ ID NO: 4 or the amino acid sequence with one or more amino acids substituted, deleted, added, and/or inserted, and a heavy-chain CDR3 consisting of the amino acid sequence set forth in SEQ ID NO: 5 or the amino acid sequence with one or more amino acids substituted, deleted, added, and/or inserted, and a light-chain CDR1 consisting of the amino acid sequence set forth in SEQ ID NO: 8 or the amino acid sequence with one or more amino acids substituted, deleted, added, and/or inserted, a light-chain CDR2 consisting of the amino acid sequence set forth in SEQ ID NO: 9 or the amino acid sequence with one or more amino acids substituted, deleted, added, and/or inserted, and a light-chain CDR3 consisting of the amino acid sequence set forth in SEQ ID NO: 10 or the amino acid sequence with one or more amino acids substituted, deleted, added, and/or inserted;

(B) comprising a heavy-chain complementarity determining region (CDR) 1 consisting of the amino acid sequence set forth in SEQ ID NO: 13 or the amino acid sequence with one or more amino acids substituted, deleted, added, and/or inserted, a heavy-chain CDR2 consisting of the amino acid sequence set forth in SEQ ID NO: 14 or the amino acid sequence with one or more amino acids substituted, deleted, added, and/or inserted, and a heavy-chain CDR3 consisting of the amino acid sequence set forth in SEQ ID NO: 15 or the amino acid sequence with one or more amino acids substituted, deleted, added, and/or inserted, and a light-chain CDR1 consisting of the amino acid sequence set forth in SEQ ID NO: 18 or the amino acid sequence with one or more amino acids substituted, deleted, added, and/or inserted, a light-chain CDR2 consisting of the amino acid sequence set forth in SEQ ID NO: 19 or the amino acid sequence with one or more amino acids substituted, deleted, added, and/or inserted, and a light-chain CDR3 consisting of the amino acid sequence set forth in SEQ ID NO: 20 or the amino acid sequence with one or more amino acids substituted, deleted, added, and/or inserted;

(C) comprising a heavy-chain complementarity determining region (CDR) 1 consisting of the amino acid sequence set forth in SEQ ID NO: 23 or the amino acid sequence with one or more amino acids substituted, deleted, added, and/or inserted, a heavy-chain CDR2 consisting of the amino acid sequence set forth in SEQ ID NO: 24 or the amino acid sequence with one or more amino acids substituted, deleted, added, and/or inserted, and a heavy-chain CDR3 consisting of the amino acid sequence set forth in SEQ ID NO: 25 or the amino acid sequence with one or more amino acids substituted, deleted, added, and/or inserted, and a light-chain CDR1 consisting of the amino acid sequence set forth in SEQ ID NO: 28 or the amino acid sequence with one or more amino acids substituted, deleted, added, and/or inserted, a light-chain CDR2 consisting of the amino acid sequence set forth in SEQ ID NO: 29 or the amino acid sequence with one or more amino acids substituted, deleted, added, and/or inserted, and a light-chain CDR3 consisting of the amino acid sequence set forth in SEQ ID NO: 30 or the amino acid sequence with one or more amino acids substituted, deleted, added, and/or inserted; and (D) comprising a heavy-chain complementarity determining region (CDR) 1 consisting of the amino acid sequence set forth in SEQ ID NO: 33 or the amino acid sequence with one or more amino acids substituted, deleted, added, and/or inserted, a heavy-chain CDR2 consisting of the amino acid sequence set forth in SEQ ID NO: 34 or the amino acid sequence with one or more amino acids substituted, deleted, added, and/or inserted, and a heavy-chain CDR3 consisting of the amino acid sequence set forth in SEQ ID NO: 35 or the amino acid sequence with one or more amino acids substituted, deleted, added, and/or inserted, and a light-chain CDR1 consisting of the amino acid sequence set forth in SEQ ID NO: 38 or the amino acid sequence with one or more amino acids substituted, deleted, added, and/or inserted, a light-chain CDR2 consisting of the amino acid sequence set forth in SEQ ID NO: 39 or the amino acid sequence with one or more amino acids substituted, deleted, added, and/or inserted, and a light-chain CDR3 consisting of the amino acid sequence set forth in SEQ ID NO: 40 or the amino acid sequence with one or more amino acids substituted, deleted, added, and/or inserted.

Preferably, the human monoclonal antibody having characteristic (A) above further has characteristic (a) below, the human monoclonal antibody having characteristic (B) above further has characteristic (b) below, the human monoclonal antibody having characteristic (C) above further has characteristic (c) below, the human monoclonal antibody having characteristic (D) above further has characteristic (d) below:

(a) comprising a heavy-chain variable region consisting of an amino acid sequence having a sequence identity of at least 80% with the amino acid sequence set forth in SEQ ID NO: 2 and a light-chain variable region consisting of an amino acid sequence having a sequence identity of at least 80% with the amino acid sequence set forth in SEQ ID NO: 7;

(b) comprising a heavy-chain variable region consisting of an amino acid sequence having a sequence identity of at least 80% with the amino acid sequence set forth in SEQ ID NO: 12 and a light-chain variable region consisting of an amino acid sequence having a sequence identity of at least 80% with the amino acid sequence set forth in SEQ ID NO: 17;

(c) comprising a heavy-chain variable region consisting of an amino acid sequence having a sequence identity of at least 80% with the amino acid sequence set forth in SEQ ID NO: 22 and a light-chain variable region consisting of an amino acid sequence having a sequence identity of at least 80% with the amino acid sequence set forth in SEQ ID NO: 27; and (d) comprising a heavy-chain variable region consisting of an amino acid sequence having a sequence identity of at least 80% with the amino acid sequence set forth in SEQ ID NO: 32 and a light-chain variable region consisting of an amino acid sequence having a sequence identity of at least 80% with the amino acid sequence set forth in SEQ ID NO: 37.

Preferably, the human monoclonal antibody having characteristics (A) and (a) above further has characteristic (a1) below, the human monoclonal antibody having characteristics (B) and (b) above further has characteristic (b1) below, the human monoclonal antibody having characteristics (C) and (c) above further has characteristic (c1) below, and the human monoclonal antibody having characteristics (D) and (d) above further has characteristic (d1) below:

(a1) comprising a heavy chain consisting of an amino acid sequence having a sequence identity of at least 80% with the amino acid sequence set forth in SEQ ID NO: 1 and a light chain consisting of an amino acid sequence having a sequence identity of at least 80% with the amino acid sequence set forth in SEQ ID NO: 6;

(b1) comprising a heavy chain consisting of an amino acid sequence having a sequence identity of at least 80% with the amino acid sequence set forth in SEQ ID NO: 11 and a light chain consisting of an amino acid sequence having a sequence identity of at least 80% with the amino acid sequence set forth in SEQ ID NO: 16;

(c1) comprising a heavy chain consisting of an amino acid sequence having a sequence identity of at least 80% with the amino acid sequence set forth in SEQ ID NO: 21 and a light chain consisting of an amino acid sequence having a sequence identity of at least 80% with the amino acid sequence set forth in SEQ ID NO: 26; and (d1) comprising a heavy chain consisting of an amino acid sequence having a sequence identity of at least 80% with the amino acid sequence set forth in SEQ ID NO: 31 and a light chain consisting of an amino acid sequence having a sequence identity of at least 80% with the amino acid sequence set forth in SEQ ID NO: 36.

The amino acid sequences of SEQ ID NOs: 3 to 5 described in characteristic (A) above represent the amino acid sequences of heavy-chain CDR1 to CDR3, respectively of antibody 127, the amino acid sequences of SEQ ID NOs: 8 to 10 described in characteristic (A) above represent the amino acid sequences of light-chain CDR1 to CDR3, respectively of antibody 127, the amino acid sequence of SEQ ID NO: 2 described in characteristic (a) above represents the amino acid sequence of the heavy-chain variable region of antibody 127, and the amino acid sequence of SEQ ID NO: 7 represents the amino acid sequence of the light-chain variable region of antibody 127, and the amino acid sequence of SEQ ID NO: 1 described in characteristic (a1) above represents the amino acid sequence of a heavy chain (that is, a heavy-chain variable region and heavy-chain constant regions) of antibody 127, and the amino acid sequence of SEQ ID NO: 6 represents the amino acid sequence of a light chain (that is, a light-chain variable region and a light-chain constant region) of antibody 127.

Further, the amino acid sequences of SEQ ID NOs: 13 to 15 described in characteristic (B) above represent the amino acid sequences of heavy-chain CDR1 to CDR3, respectively of antibody 129, the amino acid sequences of SEQ ID NOs: 18 to 20 described in characteristic (B) above represent the amino acid sequences of light-chain CDR1 to CDR3, respectively of antibody 129, the amino acid sequence of SEQ ID NO: 12 described in characteristic (b) above represents the amino acid sequence of a heavy-chain variable region of antibody 129, and the amino acid sequence of SEQ ID NO: 17 represents the amino acid sequence of a light-chain variable region of antibody 129, and the amino acid sequence of SEQ ID NO: 11 described in characteristic (b1) above represents the amino acid sequence of a heavy chain (that is, a heavy-chain variable region and heavy-chain constant regions) of antibody 129, and the amino acid sequence of SEQ ID NO: 16 represents the amino acid sequence of a light chain (that is, a light-chain variable region and a light-chain constant region) of antibody 129.

Further, the amino acid sequences of SEQ ID NOs: 23 to 25 described in characteristic (C) above represent the amino acid sequences of heavy-chain CDR1 to CDR3, respectively of antibody 213-001, the amino acid sequences of SEQ ID NOs: 28 to 30 described in characteristic (C) above represent the amino acid sequences of light-chain CDR1 to CDR3, respectively of antibody 213-001, the amino acid sequence of SEQ ID NO: 22 described in characteristic (c) above represents the amino acid sequence of a heavy-chain variable region of antibody 213-001, and the amino acid sequence of SEQ ID NO: 27 represents the amino acid sequence of a light-chain variable region of 123-001 antibody, and the amino acid sequence of SEQ ID NO: 21 described in characteristic (c1) above represents the amino acid sequence of a heavy chain (that is, a heavy-chain variable region and heavy-chain constant regions) of antibody 213-001, and the amino acid sequence of SEQ ID NO: 26 represents the amino acid sequence of a light chain (that is, a light-chain variable region and a light-chain constant region) of antibody 213-001.

Further, the amino acid sequences of SEQ ID NOs: 33 to 35 described in characteristic (D) above represent the amino acid sequences of heavy-chain CDR1 to CDR3, respectively of antibody 213-012, the amino acid sequences of SEQ ID NOs: 38 to 40 described in characteristic (D) above represent the amino acid sequences of light-chain CDR1 to CDR3, respectively of antibody 213-012, the amino acid sequence of SEQ ID NO: 32 described in characteristic (d) above represents the amino acid sequence of a heavy-chain variable region of antibody 213-012, and the amino acid sequence of SEQ ID NO: 37 represents the amino acid sequence of a light-chain variable region of antibody 213-012, and the amino acid sequence of SEQ ID NO: 31 described in characteristic (d1) above represents the amino acid sequence of a heavy chain (that is, a heavy-chain variable region and heavy-chain constant regions) of antibody 213-012, and the amino acid sequence of SEQ ID NO: 36 represents the amino acid sequence of a light chain (that is, a light-chain variable region and a light-chain constant region) of antibody 213-012.

In the present invention, "HMGB1 (High Mobility Group Box 1)" is a protein also called HMG1, HMG3, SBP-1, or HMG-1. Examples of those derived from humans typically include a protein consisting of the amino acid sequence specified by NCBI reference sequence: NP_002119.1 (a protein encoded by the nucleotide sequence specified by NCBI reference sequence: NM_002128.5).

However, the DNA sequence of a gene is mutated in nature (that is, non-artificially) due to the mutation or the like, and the amino acid sequence of the protein encoded thereby is also modified accordingly. Therefore, "HMGB1" according to the present invention is not specified to the protein consisting of such a typical amino acid sequence but includes such a natural mutant.

In the present invention, the "antibody that specifically binds to human HMGB1" refers to an antibody that recognizes and binds to human HMGB1 by a highly specific recognition mechanism between an antigen and an antibody. The human monoclonal antibody of the present invention is preferably separated. Here, "being separated" means the antibody existing in a state different from the state where the antibody originally exists by being artificially extracted from the environment in which it originally exists or being expressed in another environment than the environment the antibody originally exists. That is, the "separated antibody" does not include an antibody derived from an individual and contained in the body of the individual, or a tissue or a body fluid (such as blood, blood plasma, and serum) derived from the body without external operation (artificial operation). Further, the human monoclonal antibody of the present invention is preferably an antibody produced from organisms or cells produced by artificial operation (for example, antibodies produced from hybridomas). The "antibody produced from organisms or cells produced by artificial operation" does not include an antibody produced from naturally occurring organisms or B cells (without artificial operation).

In the present invention, the "monoclonal antibody" refers to an antibody obtained from a substantially uniform population of antibodies (including a functional fragment of the antibody). The monoclonal antibody recognizes a single determinant on an antigen. The "antibody" in the present invention includes classes and subclasses of human immunoglobulin and further includes the form of a functional fragment of the antibody. Examples of the classes and subclasses of the human monoclonal antibody of the present invention include IgGs such as IgG1, IgG2, IgG3, and IgG4; IgAs such as IGA1 and IGA2; IgD; IgE; and IgM. Among them, IgGs and IgM are preferable.

Typically, the human monoclonal antibody of the present invention includes heavy-chain CDR1, heavy-chain CDR2, and heavy-chain CDR3, and light-chain CDR1, light-chain CDR2, and light-chain CDR3, and framework regions (FRs) are linked to the amino (N) terminal and the carboxyl (C) terminal in each region of CDR1 to CDR3. When the heavy chains and the light chains of the human monoclonal antibody of the present invention form a three-dimensional structure, these CDRs may come close to each other to give specificity for human HMGB1. Preferable examples of the specific combination of CDR1 to CDR3 include the combination described in characteristic (A) above, the combination described in characteristic (B) above, the combination described in characteristic (C) above, and the combination described in characteristic (D) above.

Of the aforementioned FRs, examples of heavy-chain FRs can include heavy-chain FR1 linked to the N-terminus of heavy-chain CDR1; heavy-chain FR2 linked between the C-terminus of heavy-chain CDR1 and the N-terminus of heavy-chain CDR2; heavy-chain FR3 linked between the C-terminus of heavy-chain CDR2 and the N-terminus of heavy-chain CDR3; and heavy-chain FR4 linked to the C-terminus of heavy-chain CDR3. Of the aforementioned FRs, examples of light-chain FRs can include light-chain FR1 linked to the N-terminus of light-chain CDR1; light-chain FR2 linked between the C-terminus of light-chain CDR1 and the N-terminus of light-chain CDR2; light-chain FR3 linked between the C-terminus of light-chain CDR2 and the N-terminus of light-chain CDR3; and light-chain FR4 linked to the C-terminus of light-chain CDR3.

Specific examples of the aforementioned heavy-chain FR1 can include a polypeptide consisting of amino acid residues at positions 1 to 30 in the amino acid sequence set forth in SEQ ID NO: 1 or a polypeptide consisting of amino acid residues at positions 1 to 30 in the amino acid sequence set forth in SEQ ID NO: 21 (HF1), or a polypeptide consisting of an amino acid sequence having a sequence identity of at least 80% with the amino acid sequence of any one of these polypeptides (HF1');

specific examples of the aforementioned heavy-chain FR2 can include a polypeptide consisting of amino acid residues at positions 36 to 49 in the amino acid sequence set forth in SEQ ID NO: 1 or a polypeptide consisting of amino acid residues at positions 36 to 49 in the amino acid sequence set forth in SEQ ID NO: 21 (HF2), or a polypeptide consisting of an amino acid sequence having a sequence identity of at least 80% with the amino acid sequence of any one of these polypeptides (HF2');

specific examples of the aforementioned heavy-chain FR3 can include a polypeptide consisting of amino acid residues at positions 67 to 98 in the amino acid sequence set forth in SEQ ID NO: 1, a polypeptide consisting of amino acid residues at positions 67 to 98 in the amino acid sequence set forth in SEQ ID NO: 11, or a polypeptide consisting of amino acid residues at positions 67 to 98 in the amino acid sequence set forth in SEQ ID NO: 21 (HF3), or a polypeptide consisting of an amino acid sequence having a sequence identity of at least 80% with the amino acid sequence of any one of these polypeptides (HF3'); and specific examples of the aforementioned heavy-chain FR4 can include a polypeptide consisting of amino acid residues at positions 117 to 127 in the amino acid sequence set forth in SEQ ID NO: 1, a polypeptide consisting of amino acid residues at positions 105 to 115 in the amino acid sequence set forth in SEQ ID NO: 11, or a polypeptide consisting of amino acid residues at positions 104 to 114 in the amino acid sequence set forth in SEQ ID NO: 21 (HF4), or a polypeptide consisting of an amino acid sequence having a sequence identity of at least 80% with the amino acid sequence of any one of these polypeptides (HF4').

Specific examples of the aforementioned light-chain FR1 can include a polypeptide consisting of amino acid residues at positions 1 to 23 in the amino acid sequence set forth in SEQ ID NO: 6 or a polypeptide consisting of amino acid residues at positions 1 to 23 in the amino acid sequence set forth in SEQ ID NO: 26 (LF1), or a polypeptide consisting of an amino acid sequence having a sequence identity of at least 80% with the amino acid sequence of any one of these polypeptides (LF1');

specific examples of the aforementioned light-chain FR2 can include a polypeptide consisting of amino acid residues at positions 35 to 49 in the amino acid sequence set forth in SEQ ID NO: 6 (LF2), or a polypeptide consisting of an amino acid sequence having a sequence identity of at least 80% with the amino acid sequence of this polypeptide (LF2');

specific examples of the aforementioned light-chain FR3 can include a polypeptide consisting of amino acid residues at positions 57 to 88 in the amino acid sequence set forth in SEQ ID NO: 6 or a polypeptide consisting of amino acid residues at positions 57 to 88 in the amino acid sequence set forth in SEQ ID NO: 26 (LF3), or a polypeptide consisting of an amino acid sequence having a sequence identity of at least 80% with the amino acid sequence of any one of these polypeptides (LF3');

specific examples of the aforementioned light-chain FR4 can include a polypeptide consisting of amino acid residues at positions 98 to 107 in the amino acid sequence set forth in SEQ ID NO: 6 or a polypeptide consisting of amino acid residues at positions 98 to 107 in the amino acid sequence set forth in SEQ ID NO: 26 (LF4), or a polypeptide consisting of an amino acid sequence having a sequence identity of at least 80% with the amino acid sequence of any one of these polypeptides (LF4').

The human monoclonal antibody of the present invention is a human antibody. In the present invention, the "human antibody" includes a human chimeric antibody, a humanized antibody, and a full human antibody. Among them, a humanized antibody and a full human antibody are preferable.

In the present invention, the "human chimeric antibody" refers to an antibody in which a variable region of an antibody derived from a non-human animal (for example, a non-human mammal such as a chicken, a mouse, a rat, or a cow) and a constant region of an antibody derived from a human are linked. A human chimeric antibody can be obtained, for example, by immunizing a nonhuman animal (preferably a non-human mammal) with an antigen, excising an antibody variable portion (variable region) that binds to the antigen from the gene of a mouse monoclonal antibody, binding the portion to the gene of an antibody constant portion (constant region) derived from human bone marrow, and incorporating it into an expression vector to be introduced into a host for production (for example, Japanese unexamined Patent Application Publication No. 08-280387, and U.S. Pat. Nos. 4,816,397, 4,816,567, and 5,807,715).

Examples of the human constant region of the human chimeric antibody include Cγ1, Cγ2, Cγ3, Cγ4, Cμ, Cδ, Cα1, Cα2, and Cε in the heavy chain, and examples thereof include Cκ and Cλ in the light chain. The amino acid sequences of these constant regions and the nucleotide sequences encoding them are known. Further, one or more amino acids in the human-derived antibody constant region can be substituted, deleted, added, and/or inserted, in order to improve the stability of the antibody itself or the stability of antibody production.

In the present invention, the "humanized antibody" refers to an antibody in which the gene sequence of an antigen-binding site (CDR) of an antibody derived from a nonhuman animal (for example, a non-human mammal such as a chicken, a mouse, a rat, or a cow) is transplanted (CDR grafted) into a human-derived antibody gene, and the production method thereof such as overlap extension PCR is known (for example, European Patent Application Publication No. 239400, European Patent Application Publication No. 125023, International Publication No. WO 90/07861, and International Publication No. WO 96/02576). The variable regions of an antibody are usually composed of three CDRs interposed between four framework regions (FRs). CDRs are regions that substantially determine the binding specificity of the antibody. While amino acid sequences of CDRs are rich in diversity, amino acid sequences constituting FRs often exhibit high homology even between antibodies with different binding specificities. Therefore, it is generally said that the binding specificity of one antibody can be transplanted into another antibody by transplanting CDRs. Further, in transplantation of non-human-derived CDRs into human FRs, human FRs having high homology with the nonhuman animal-derived FRs are selected for maintaining the functions of CDRs. That is, amino acids in CDRs not only recognize antigens but also coordinate with amino acids in FRs in the vicinity of the CDRs and are involved in maintaining the loop structure of the CDRs. Therefore, it is preferable to use human FRs consisting of amino acid sequences having high homology with the amino acid sequences of FRs adjacent to the CDRs to be transplanted.

Known human FRs having high homology with nonhuman animal-derived FRs can be searched for, for example, using a search system (www.bioinf.org.uk/abysis/) specialized for antibodies available on the internet. Mutations can be introduced into sequences other than the CDRs of the non-human-derived antibody so as to match the sequences of the human FRs thus obtained. Alternatively, when genes (cDNAs) encoding the amino acid sequences of the human FRs obtained by the search are available, the non-human-derived CDRs may be introduced into the sequences. The mutations or the like can be introduced using techniques known in the art such as nucleic acid synthesis and site-specific mutagenesis.

FRs of a human-derived antibody such that the CDRs form good antigen-binding sites when linked via the CDR can be suitably selected by qualitatively or quantitatively measuring and evaluating the affinity of the humanized antibody thus produced for an antigen. If necessary, amino acid residues of FRs may be substituted by the method according to Sato, K. et al., Cancer Res, 1993, 53, 851-856, or the like, so that the CDRs of the humanized antibody form appropriate antigen-binding sites, and mutant FR sequences having desired properties can be selected by further measuring and evaluating the affinity of such a mutant antibody with amino acids substituted for an antigen.

In the present invention, the "full human antibody" refers to an antibody in which all sequences of the antibody are derived from humans. The full human antibody can be produced, for example, in transgenic mice engineered to express the human heavy- and light-chain antibody genes. Methods for preparing transgenic mice that produce a human antibody are described, for example, in International Publication No. WO 02/43478 and U.S. Pat. No. 6,657,103 (Abgenix). Then, B cells derived from transgenic mice that produce a desired antibody can be fused therewith to produce hybridoma cell lines for continuously producing the antibody. See U.S. Pat. Nos. 5,569,825; 5,625,126; 5,633, 425; 5,661,016; and 5,545,806; and Jakobovits, Adv. Drug Del. Rev. 31: 33-42 (1998); and Green, et al, J. Exp. Med. 188: 483-95 (1998), for example.

As described above, the human monoclonal antibody of the present invention includes an antibody consisting of the whole antibody, as well as a functional fragment that is a part (partial fragment) of the antibody and specifically recognizes HMGB1 protein. Examples of the functional fragment include Fab, Fab', F(ab')$_2$, a variable region fragment (Fv), a disulfide bond Fv, a single-chain Fv (scFv), sc (Fv)$_2$, a diabody, a multispecific antibody, and a polymer of these.

Here, the "Fab" means a monovalent antigen-binding fragment of immunoglobulin consisting of one light chain and a part of a heavy chain. It can be obtained by papain digestion of the antibody or by a recombinant method. The "Fab'" is different from the Fab due to the addition of a few residues at the carboxy terminus of the heavy-chain CH1 domain including one or more cysteines in the hinge region of the antibody. The "F(ab')2" means a divalent antigen-binding fragment of immunoglobulin consisting of parts of both light chains and both heavy chains.

The "variable region fragment (Fv)" is the smallest antibody fragment with complete antigen recognition and a binding site. The Fv is a dimer in which a heavy-chain variable region and a light-chain variable region are strongly linked by a non-covalent bond. The "single-chain Fv (scFv)" includes a heavy-chain variable region and a light-chain variable region of the antibody, and these regions are present on a single polypeptide chain. The "sc (Fv)2" is a single chain formed by binding two heavy-chain variable regions and two light-chain variable regions with linkers or the like. The "diabody" refers to a small antibody fragment having two antigen-binding sites, the fragment includes a heavy-chain variable region that binds to a light-chain variable region in the same polypeptide chain, and each region forms a pair with a complementary region of another chain. The "multispecific antibody" is a monoclonal antibody having binding specificities for at least two different antigens. For example, it can be prepared by simultaneous expression of two immunoglobulin heavy/light-chain pairs in which the two heavy chains have different specificities.

The human monoclonal antibody of the present invention includes a human monoclonal antibody with its amino acid sequence modified without reducing desirable activities (affinity to antigens and/or other biological properties). Such amino acid sequence mutants can be produced, for example, by mutagenesis into DNA encoding the antibody chains of antibody 127, antibody 129, antibody 213-001, or antibody 213-012, or peptide synthesis. Such modification, for example, includes substitution, deletion, addition, and/or insertion of residues in the amino acid sequence of the human monoclonal antibody. The site where the amino acid sequence of the human monoclonal antibody is modified may be a constant region or a variable region (such as a FR and a CDR) in the heavy or light chain of the antibody, as long as the human monoclonal antibody has the same activity (preferably, the inhibitory activity on phosphorylation of Ser46 of human MARCKS) as before modification but is preferably a constant region. Modification of amino acids other than those in CDRs is considered to have a relatively small effect on the antigen affinity, and methods of screening for antibodies with enhanced antigen affinity by modifying amino acids in CDRs are currently known (PNAS, 102: 8466-8471 (2005), Protein Engineering, Design & Selection, 21: 485-493 (2008), International Publication No. WO 2002/051870, J. Biol. Chem., 280: 24880-24887 (2005), Protein Engineering, Design & Selection, 21:345-351 (2008), and MAbs. Mar-Apr; 6 (2): 437-45 (2014)). Nowadays, it is also possible to model antibodies with enhanced antigen affinity using an integrated computational chemistry system (for example, Molecular Operating Environment, manufactured by Chemical Computing Group, Canada) (for example, (for example, see www.rsi-.co.jp/kagaku/cs/ccg/products/application/protein.html).

Further, it is known that CDR1 in the heavy-chain variable region and CDR3 in the light-chain variable region are not involved in the antigen affinity, as described in Protein Eng Des Sel. 2010 Aug; 23 (8): 643-51. Likewise, Molecular Immunology 44: 1075-1084 (2007)) reports that, in most antibodies, CDR2 in the light-chain variable region is not involved in the antigen affinity. In this way, the same activity can be exerted on the antigen affinity of antibodies without requiring all of CDR1 to CDR3 in each of the heavy-chain variable region and the light-chain variable region. Actually, Biochem Biophys Res Commun. 2003 Jul. 18; 307 (1): 198-205, J Mol Biol. 2004 Jul. 9; 340 (3): 525-42, and J Mol Biol. 2003 Aug. 29; 331 (5): 1109-20 have reported that the antigen affinity was maintained by retaining at least one CDR of the original antibody. Accordingly, the human monoclonal antibody of the present invention can be an antibody containing at least one CDR of any one antibody selected from the group consisting of antibody 127, antibody 129, antibody 213-001, and antibody 213-012.

Further, the number of amino acids to be modified in the human monoclonal antibody of the present invention is preferably within ten amino acids, more preferably within five amino acids, further preferably within three amino acids (for example, within two amino acids or one amino acid). That is, the "plurality of amino acids" in this description preferably refer to ten or less amino acids, more preferably five or less amino acids, further preferably three or less amino acids, more preferably two or less amino acids. The modification of amino acids is preferably a conservative substitution. In the present invention, the "conservative substitution" refers to substitution with other amino acid residues having chemically similar side chains. Groups of amino acid residues having chemically similar side chains are well known in the art to which the present invention belongs. For example, they can be classified into acidic amino acids (such as aspartic acid and glutamic acid), basic amino acids (such as lysine, arginine, and histidine), neutral amino acids including amino acids having hydrocarbon chains (such as glycine, alanine, valine, leucine, isoleucine, and proline), amino acids having hydroxy groups (such as serine and threonine), amino acids containing sulfur (such as cysteine and methionine), amino acids having amide groups (such as asparagine and glutamine), amino acids having imino groups (such as proline), and amino acids having aromatic groups (such as phenylalanine, tyrosine, and tryptophan).

As described above, the human monoclonal antibody of the present invention also includes a human monoclonal antibody (including a functional fragment of an antibody) comprising a heavy-chain variable region consisting of an amino acid sequence having a sequence identity of at least 80% with a predetermined amino acid sequence, and a light-chain variable region consisting of an amino acid sequence having a sequence identity of at least 80% with a predetermined amino acid sequence. The sequence identity may be at least 80%, but preferably 85% or more, more preferably 90% or more, still more preferably 95% or more (for example, 96% or more, 97% or more, 98% or more, 99% or more, or 100%). The sequence homology can be determined using a BLASTP (amino acid level) program (Altschul et al. J. Mol. Biol., 215: 403-410, 1990). This program is based on the algorithm BLAST (Proc. Natl. Acad. Sci. USA, 87: 2264-2268, 1990, Proc. Natl. Acad. Sci. USA, 90: 5873-5877, 1993) by Karlin and Altschul. When analyzing an amino acid sequence by BLASTP, parameters are set, for example, to score=50 and wordlength=3. Further, an amino acid sequence can be analyzed using the Gapped BLAST program as described in Altschul, et al. (Nucleic Acids Res. 25: 3389-3402, 1997). In the case of using the BLAST and the Gapped BLAST program, default parameters for each program are used. Specific techniques of these analysis methods are known.

Further, "having the same activity" means that the inhibitory activity on phosphorylation of Ser46 of human MARCKS equivalent (for example, 70% or more, preferably 80% or more, more preferably 90% or more, further preferably 95% or more, more preferably 100% or more) to that of the target antibody (typically, any one antibody selected from the group consisting of antibody 127, antibody 129, antibody 213-001, and antibody 213-012). Further, the inhibitory activity on phosphorylation of Ser46 of human MARCKS can be appropriately evaluated by those skilled in the art, for example, by Western blotting or the like using an antibody that specifically binds to human HMGB1 with Ser46 phosphorylated, as in Example 4, which will be described below. The nucleotide sequence and the amino acid sequence of human MARCKS are known (Genbank accession number M68956.1), and those skilled in the art would be able to produce a human MARCKS protein by a known method.

Further, the modification of the human monoclonal antibody of the present invention may be a modification of a process after translation of the antibody such as a change of the number or positions of the glycosylation sites. This can improve, for example, the ADCC activity of the antibody (antibody-dependent cellular cytotoxicity). The antibody glycosylation is typically N- or O-linkage. The antibody glycosylation significantly depends on the host cell used for expressing the antibody. A glycosylation pattern can be modified by a known method such as introduction or deletion of a specific enzyme involved in sugar production (Japanese unexamined Patent Application Publication No. 2008-113663, U.S. Pat. Nos. 5,047,335, 5,510,261, 5,278, 299, and International Publication No. WO 99/54342). In the present invention, deamidation may be suppressed for increasing the stability of the antibody by substitution of the amino acid to be deamidated or an amino acid adjacent to the amino acid to be deamidated with another amino acid. Further, it is also possible to increase the stability of the antibody by substituting a glutamic acid with another amino acid. The present invention also provides an antibody thus stabilized.

The human monoclonal antibody of the present invention can be produced by a known hybridoma method or a known recombinant DNA method. Examples of the hybridoma method typically include Kohler & Milstein method (Kohler & Milstein, Nature, 256: 495 (1975)). The antibody-producing cells used in the cell fusion step of this method are spleen cells, lymph node cells, peripheral blood leukocytes, and the like of an animal (for example, a mammal such as a mouse, a rat, a hamster, a rabbit, a monkey, or a goat) immunized with an antigen (such as HMGB1 protein, its partial peptide, a protein in which they are fused with Fc protein, or cells expressing them). It is also possible to use antibody-producing cells obtained by allowing an antigen to act in a medium against the above-mentioned cells or lymphocytes isolated in advance from a non-immunized animal. Various known cell lines can be used as myeloma cells. The antibody-producing cells and myeloma cells may be derived from different animal species, as long as they can be fused together, but are preferably derived from the same animal species. Hybridomas are produced, for example, by cell fusion between spleen cells obtained from mice immunized with an antigen and mouse myeloma cells, and hybridomas that produce monoclonal antibodies specific for HMGB1 protein can be obtained by subsequent screening. Human monoclonal antibodies that bind specifically to HMGB1 protein can be obtained by culturing hybridomas and from the ascites of mammals to which the hybridomas have been administered.

The recombinant DNA method is a technique to produce the human monoclonal antibody of the present invention as a recombinant antibody by cloning an antibody gene encoding the human monoclonal antibody of the present invention from hybridomas, B cells, or the like, incorporating it into a suitable vector, and introducing it into a host cell (for example, a mammalian cell line such as HEK cells, Escherichia coli, yeast cells, insect cells, and plant cells) (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). In the expression of the antibody gene encoding the human monoclonal antibody of the present invention, an antibody gene encoding a heavy chain or a light chain may be separately incorporated into an expression vector to transform the host cell, or an antibody gene encoding a heavy chain and a light chain may be incorporated into a single expression vector to transform the host cell (see International Publication No. WO 94/11523). The human monoclonal antibody of the present invention can be obtained in substantially pure and uniform form by culturing the aforementioned host cell and separating and purifying the antibody in the host cell or from the culture medium. The method used in the usual purification of a polypeptide can be used for separating and purifying the antibody. If a transgenic animal with the antibody gene of the present invention incorporated is produced using a transgenic animal production technique, a large amount of human monoclonal antibody derived from the antibody gene can be obtained from milk of a transgenic animal (such as a cow, a goat, a sheep, and a pig).

<Composition Comprising Human Monoclonal Antibody that Specifically Binds to HMGB1>

The composition comprising the human monoclonal antibody of the present invention is not specifically limited as long as the composition comprises the human monoclonal antibody of the present invention. In such a composition, examples of the substance other than the human monoclonal antibody include a carrier such as water and a stabilizer.

As will be described in Examples below, the human monoclonal antibody of the present invention exhibits a high affinity for human HMGB1 protein and also has a high inhibitory activity on phosphorylation of Ser46 of human MARCKS. The inventors have confirmed that a mouse monoclonal antibody against HMGB1 that inhibits phosphorylation of Ser46 of human MARCKS restores cognitive impairment in Alzheimer's disease model mice, reduces DNA damage in the cerebral cortex, and inhibits multimer formation of both Aβ and HMGB1 (Non Patent Document 2 and Patent Document 3). In consideration of these findings, it can be said that the human monoclonal antibody of the present invention can be used for treating or preventing human Alzheimer's disease. Accordingly, the present invention also provides: a pharmaceutical composition for treating or preventing Alzheimer's disease, comprising the human monoclonal antibody of the present invention as an active component; and a method for treating or preventing Alzheimer's disease, comprising a step of administering a therapeutically or prophylactically effective amount of the human monoclonal antibody of the present invention to a human.

In the present invention, "Alzheimer's disease" refers to a neurodegenerative disease also called Alzheimer-type dementia or AD, and it also includes "familial Alzheimer's disease" and "hereditary Alzheimer's disease" caused by gene mutations, and "sporadic Alzheimer's disease" caused by environment factors such as lifestyle and stress. Further, "Alzheimer's disease" also includes not only the stage where clinical symptoms including expression of symptoms such as memory impairment, cognitive impairment, higher brain dysfunction (aphasia, apraxia, agnosia, and constructional apraxia), and personality changes, appearance of brain atrophy determined by diagnostic imaging are observed but also mild cognitive impairment (MCI), which is considered to be the pre-stage, and preclinical Alzheimer's disease (preclinical AD) further prior to the pre-stage, in which the cognitive function is normal, but amyloid β (Aβ) aggregates (amyloid lesions) occur in the brain. Further, treatment of Alzheimer's disease includes not only recovery and improvement of Alzheimer's disease lesions including amyloid lesions, but also suppression of progression thereof.

The pharmaceutical composition of the present invention can be used in the form of a composition containing the human monoclonal antibody of the present invention and optional ingredients such as saline, a glucose aqueous solution, or a phosphate buffer. The pharmaceutical composition of the present invention may be prepared in liquid or lyophilized form, as needed, and may optionally contain a pharmaceutically acceptable carrier or medium such as a stabilizer, a preservative, and an isotonic agent.

Examples of the pharmaceutically acceptable carrier can include mannitol, lactose, saccharose, and human albumin, in the case of a lyophilized preparation, and can include saline, water for injection, a phosphate buffer, and aluminum hydroxide, in the case of a liquid preparation, but there is no limitation to these examples.

The method for administering the pharmaceutical composition of the present invention differs depending on the age, body weight, gender, health conditions, or the like of the administration target, but any one administration route of parenteral administration (such as subcutaneous administration, intravenous administration, arterial administration, and topical administration) and oral administration can be selected. The administration method is preferably parenteral administration, more preferably subcutaneous administration or intravenous administration. The dose of the pharmaceutical composition may vary depending on the patient's age, body weight, gender, health conditions, and degree of progression of symptoms, and ingredients of the pharmaceutical composition to be administered, but the daily dose for adults is generally 0.1 to 1000 mg, preferably 1 to 100 mg per kg of body weight. The pharmaceutical composition of the present invention may be used in combination with known pharmaceutical products used for treating Alzheimer's disease.

<Antibody Gene Encoding Human Monoclonal Antibody of Present Invention>

The antibody gene encoding the human monoclonal antibody of the present invention is not particularly limited, as long as it is an antibody gene encoding the human monoclonal antibody of the present invention. Specific examples thereof can include an antibody gene consisting of a nucleotide sequence encoding the amino acid sequence of the human monoclonal antibody of the present invention. The human monoclonal antibody of the present invention encoded by the antibody gene of the present invention may be any one of the aspects of the human monoclonal antibody of the present invention described in <Human Monoclonal Antibody of the Present Invention> above. Specific examples of the human monoclonal antibody of the present invention include the following antibodies (including functional fragments of the antibodies):

a human monoclonal antibody that binds specifically to human HMGB1 and has characteristic (A) above;

a human monoclonal antibody that binds specifically to human HMGB1 and has characteristic (B) above;

a human monoclonal antibody that binds specifically to human HMGB1 and has characteristic (C) above;

a human monoclonal antibody that binds specifically to human HMGB1 and has characteristic (D) above;

a human monoclonal antibody that binds specifically to human HMGB1 and has characteristics (A) and (a) above;

a human monoclonal antibody that binds specifically to human HMGB1 and has characteristics (B) and (b) above;

a human monoclonal antibody that binds specifically to human HMGB1 and has characteristics (C) and (c) above;

a human monoclonal antibody that binds specifically to human HMGB1 and has characteristics (D) and (d) above;

a human monoclonal antibody that binds specifically to human HMGB1 and has characteristics (A), (a), and (a1) above;

a human monoclonal antibody that binds specifically to human HMGB1 and has characteristics (B), (b), and (b1) above;

a human monoclonal antibody that binds specifically to human HMGB1 and has characteristics (C), (c), and (c1) above;

and a human monoclonal antibody that binds specifically to human HMGB1 and has characteristics (D), (d), and (d1) above.

For the nucleotide sequence of the antibody gene of the present invention, those skilled in the art would be able to specifically and clearly grasp the nucleotide sequence corresponding to the amino acid sequence of the human monoclonal antibody of the present invention by referring to the amino acid sequence and a known codon table.

<Vector and Host Cell of Present Invention>

The vector of the present invention is not specifically limited, as long as it is a vector comprising a promoter and the antibody gene of the present invention operably linked downstream of the promoter. A vector for the vector of the present invention, and the vector of the present invention can be appropriately selected corresponding to the type of the host cell (or host organism) into which the vector of the present invention is to be introduced.

In the case of using a mammalian cell (such as a human-derived Namalwa cell, a monkey-derived COS cell, and a Chinese hamster ovary-derived CHO cell) as a host cell, examples of the vector of the present invention can include a vector such as pcDNAI, pcDM8 (manufactured by Funakoshi Co., Ltd.), pAGE107 (Japanese unexamined Patent Application Publication No. 03-22979; Cytotechnology, 3, 133 (1990)), pAS3-3 (Japanese unexamined Patent Application Publication No. 02-227075), pCDM8 (Nature, 329, 840 (1987)), pcDNAI/Amp (manufactured by Invitrogen), pREP4 (manufactured by Invitrogen), pAGE103 (J. Biochemistry, 101, 1307(1987)), and pAGE210, or those derived from such vectors, and examples of the promoter can include a promoter of the IE (immediate early) gene of cytomegalovirus (CMV), an early promoter of SV40, a promoter of retrovirus, a metallothionein promoter, a heat shock promoter, and an SRα promoter.

For further enhancing the gene expression efficiency, the vector of the present invention preferably further contains the nucleotide sequence of an enhancer region or a ribosome-binding site (RBS). For screening the host cell of the present invention, the vector of the present invention preferably further contains a drug-resistant gene corresponding to the type of the host cell (such as a spectinomycin-resistant gene, a chloramphenicol-resistant gene, a tetracycline-resistant gene, a kanamycin-resistant gene, an ampicillin-resistant gene, a puromycin-resistant gene, a hygromycin-resistant gene, a blasticidin-resistant gene, and a genetiin-resistant gene). The enhancer region is generally located upstream of the promoter, and the RBS is generally located between the promoter and the gene of the present invention. The nucleotide sequence of the antibody gene of the present invention to be incorporated into the vector of the present invention may have a codon sequence optimized according to the host cell to be expressed. The vector of the present invention can be produced by a known method using a gene recombination technology.

The species of the host cell of the present invention may be any species, as long as the mRNA of the antibody gene of the present invention is transcribed, and the antibody protein of the present invention is expressed. Examples thereof include a mammal (such as a human, a mouse, a rat, and a monkey) and a yeast (such as *Saccharomyces cerevisiae* and *Schizosaccharomyces pombe*). Among them, a mammal is preferable.

The hybridomas that produce the human monoclonal antibody of the present invention may be cells (fusion cells) obtained by fusing two or more cells (preferably mammalian cells) that produce the antibody of the present invention and are preferably fusion cells of B cells that produce the human monoclonal antibody of the present invention and cells having growth ability (such as myeloma cells).

The host cell of the present invention can be obtained by introducing (transfecting) the vector of the present invention into a host cell by a method corresponding to the type of the host cell.

In the case of using the aforementioned mammalian cell as the host cell, the method for introducing the vector of the present invention into the mammalian cell may be a method for introducing DNA into a mammalian cell. Examples thereof can include the electroporation method (Cytotechnology, 3, 133 (1990)), the calcium phosphate method (Japanese unexamined Patent Application Publication No. 02-227075), and the lipofection method (Proc. Natl. Acad. Sci. U.S.A., 84, 7413 (1987)).

The aspects of the present invention also include a method for producing the human monoclonal antibody of the present invention, comprising culturing the host cell comprising the vector of the present invention introduced thereinto, and collecting the human monoclonal antibody of the present invention.

Hereinabove, suitable embodiments (applications) of the antibody of the present invention have been described, but the antibody of the present invention is not limited to the aforementioned embodiments. With a high affinity for human HMGB1 protein, the antibody of the present invention is suitably used, for example, as a reagent and a diagnostic agent for detecting human HMGB1 protein.

When used as a reagent and a diagnostic agent for detecting human HMGB1 protein, the human monoclonal antibody of the present invention may be directly or indirectly bound with a labeling substance for the detection. Examples of the labeling substance include a radioisotope, a fluorescent substance, and a luminescent substance.

Hereinafter, the present invention will be described more specifically based on Examples, but the present invention is not limited to Examples below.

Example 1

Production of Anti-Human HMGB1 Monoclonal Antibody

Using the ADLib (R) system (manufactured by Chiome Bioscience Inc.), a human monoclonal antibody that specifically recognizes human HMGB1 protein was produced. Specifically, a full-length human HMGB1 protein (manufactured by HMGBiotech) was first immobilized on magnetic beads. The aforementioned magnetic beads were added to a human antibody gene cell library constructed by incorporating a human immunoglobulin gene into DT40 cells (chicken B lymph cell line). Cells producing the antibody that recognizes human HMGB1 protein (which will be hereinafter referred to as "antibody-producing cells") were bound to the magnetic beads by incubation for about 30 minutes, and thereafter the magnetic beads were attracted by a magnet to collect the magnetic beads and the antibody-producing cells bound thereto. The plurality of antibody-producing cells obtained were cultured for about one week to proliferate, and the human IgG antibody secreted into each culture medium was isolated and obtained. The human monoclonal antibodies thus produced were named "#127", "#129", "#194", "#459", "#130-008", "#213-012", "#213-001", "#283-010", and "#370-010" (these nine kinds or some of monoclonal antibodies may be collectively referred to as "the human monoclonal antibody group of the present invention").

Example 2

Analysis of Antibody-Binding Ability by Western Blotting

The binding abilities of the human monoclonal antibodies of the present invention to human HMGB1 were compared and examined using Western blotting. Specifically, 2.5 μL of a sample buffer (125 mM Tris-HCl (pH 6.8, manufactured by Sigma-Aldrich Co. LLC.), 4% SDS (manufactured by Sigma-Aldrich Co. LLC.), 10% glycerol (manufactured by Sigma-Aldrich Co. LLC.), 5% mercapto ethanol (manufactured by FUJIFILM Wako Pure Chemical Corporation), and 0.05% BPB (manufactured by Sigma-Aldrich Co. LLC.)) were added to 2.5 μL of 1.0 μg/μL disulfide HMGB1 (manufactured by HMGBiotech), followed by heating at 100° C. for 5 minutes, to prepare an HMGB1 sample for SDS-PAGE. SDS-PAGE was performed using such a sample (2.5 μg of disulfide HMGB1 was loaded per lane), and the sample was transcribed into an Immobilon (R)-P polyvinylidene fluoride membrane (EMD Millipore Corporation) by the semi-dry method, followed by blocking treatment with 2% BSA (manufactured by NACALAI TESQUE, INC.)—or 5% milk-containing TBST (10 mM Tris-HCl, pH 8.0, 150 mM NaCl, 0.05% Tween-20).

Then, the human monoclonal antibody group of the present invention and a commercially available anti-human HMGB1 antibody (positive control) were each diluted to a concentration of 1.0 μg/mL using TBST containing 0.2% BSA or an immunoreaction enhancer solution (Can Get Signal (R), manufactured by TOYOBO CO., LTD.), to prepare a primary antibody solution. Further, an HRP-labeled anti-human IgG antibody (manufactured by MBL) was diluted to 1:3000 times using TBST containing 0.2% BSA or an immunoreaction enhancer solution, to prepare a secondary antibody solution. The aforementioned membrane was incubated together with the primary antibody solution at 4° C. overnight, washed, and then incubated together with the secondary antibody solution at room temperature for 1 hour. The membrane after incubation was washed, and an ECL Select Western blot detection reagent (manufactured by GE Healthcare) and a lumino image analyzer (ImageQuant LAS 500, manufactured by GE Healthcare) were used to detect a signal in each lane.

FIG. 1 shows the results. In each of the lanes using monoclonal antibodies #129 and #213-001, a strong signal was detected at the position corresponding to the molecular weight of the HMGB protein, similar to the commercially available anti-human HMGB1 antibody. Also in each of the lanes using monoclonal antibodies #194, #213-012, #283-010, and #370-010, a weak signal was detected at the same position. Meanwhile, in each of the lanes using monoclonal antibodies #127, #459, and #130-008, no signal was detected.

Example 3

Analysis of Antibody Affinity by Surface Plasmon Resonance Spectroscopy (SPR)

Figure 2:
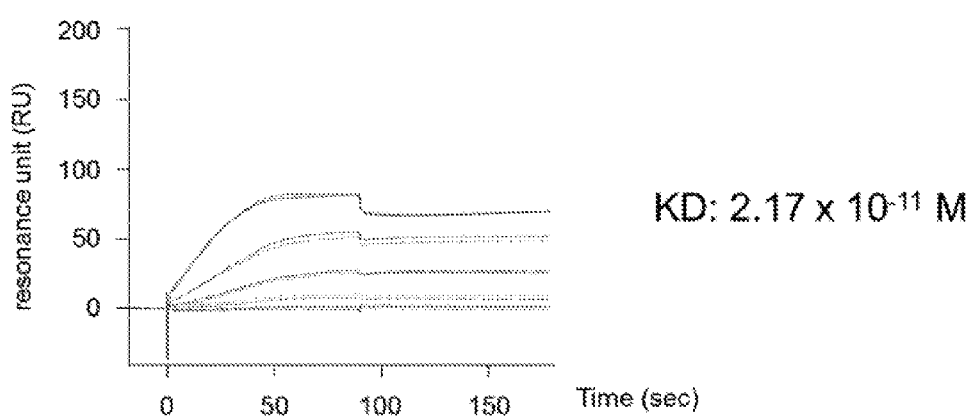
FIG. 2 shows the examination results of the interaction between a human monoclonal antibody of the present invention (monoclonal antibody #127) and human HMGB1 protein by surface plasmon resonance spectroscopy (SPR). As a result of the analysis, the dissociation constant (KD) of monoclonal antibody #127 was $2.17 \times 10^{-11}$ M, revealing that the antibody had an extremely high affinity.
Figure 3:
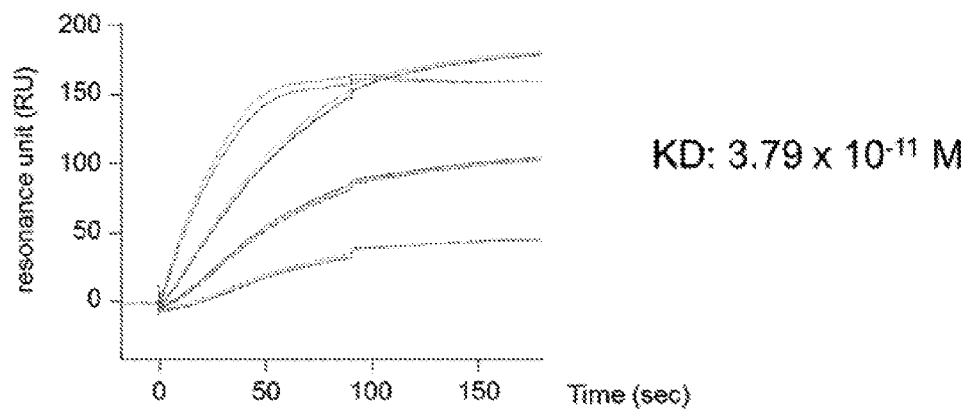
FIG. 3 shows the examination results of the interaction between a human monoclonal antibody of the present invention (monoclonal antibody #129) and human HMGB1 protein by SPR. As a result of the analysis, the dissociation constant (KD) of monoclonal antibody #129 was $3.79 \times 10^{-11}$ M, revealing that the antibody had an extremely high affinity.
Figure 4:
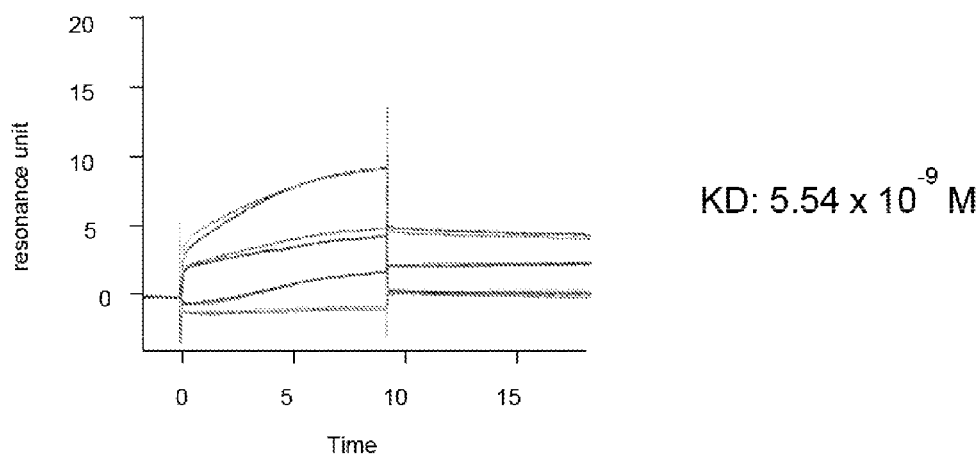
FIG. 4 shows the examination results of the interaction between a human monoclonal antibody of the present invention (monoclonal antibody #213-001) and human HMGB1 protein by SPR. As a result of the analysis, it turned out that the dissociation constant (KD) of monoclonal antibody #213-001 was $5.54 \times 10^{-9}$ M.

The interaction between the human monoclonal antibody group of the present invention and human HMGB1 protein was compared and examined using SPR. Specifically, using a sensor chip on which each human monoclonal antibody of the present invention was immobilized and human HMGB1 protein as an analyte, the interaction was measured over time with a surface plasmon resonance sensor ("Biacore T100", manufactured by GE healthcare), to calculate an equilibrium dissociation constant (KD value) as an index of the antibody affinity. FIGS. 2 to 4 show the resultant typical sensorgrams. Of the human monoclonal antibodies of the present invention, the KDs of monoclonal antibodies #127, #129, and #213-001 were $2.17 \times 10^{-11}$ M, $3.79 \times 10^{-11}$ M, and $5.54 \times 10^{-9}$ M, respectively. Considering that the KD of a common antibody drug is $10^{-9}$ M to $10^{-10}$ M, it can be said that antibodies #127 and #129 had extremely high affinity, and antibody #213-001 also had sufficiently high affinity.

Further, in the Western blot analysis of Example 2, HMGB1 protein could not be detected even using monoclonal antibody #127. It is presumed that such differences in the results are due to differences in the method for adjusting the HMGB1 protein (antigen) used in the experiment. That is, it is considered from the results of Examples 2 and 3 that monoclonal antibody #127 cannot bind to HMGB1 protein degenerated for SDS-PAGE but can bind to HMGB1 protein maintaining a higher-order structure with high affinity.

Example 4

Examination of Human MARCKS Phosphorylation Inhibitory Activity of Human Monoclonal Antibody Group of Present Invention Previous studies by the inventors have revealed that phosphorylation of MARCKS protein in the brain occurs before the onset of Alzheimer's disease (Non Patent Document 1), and such phosphorylation is induced by HMGB1 (Non Patent Document 2). In Example 4, whether or not the human monoclonal antibody group of the present invention exerts an inhibitory effect on such phosphorylation of MARCKS protein by HMGB1 was compared and examined in vitro.

Figure 5:
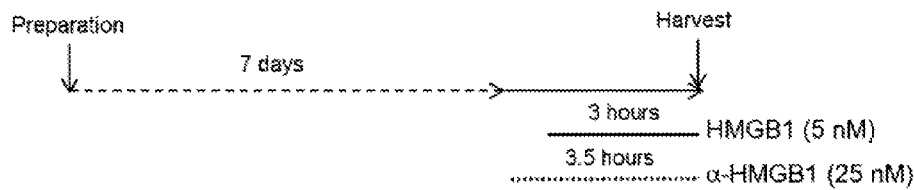
FIG. 5 shows the experiment schedule for examining the human MARCKS phosphorylation inhibitory activity of the human monoclonal antibodies of the present invention. In the figure, "Preparation" indicates the time when the primary cultured cortical neurons were collected from mouse embryo (E15), and "Harvest" indicates the time when the primary cultured cortical neurons after the culture were collected. In the figure, "α-HMGB1" represents each human monoclonal antibody of the present invention or the commercially available anti-HMGB1 antibody, and "HMGB1" represents human HMGB1 protein. In this experiment, the human monoclonal antibody of the present invention or the commercially available anti-HMGB1 antibody was added to the primary cultured cortical neurons cultured for 7 days, and then human HMGB1 protein was added thereto, to examine the effects of each antibody on MARCKS phosphorylation by HMGB1.

Specifically, primary cultured cortical neurons collected from mouse embryo (E15) were cultured for seven days, then each human monoclonal antibody of the present invention or the commercially available anti-human HMGB1 antibody (positive control) was added thereto, and human HMGB1 protein was further added thereto 30 minutes later, followed by incubation for 3 hours (FIG. 5). The cells after incubation were collected, and a lysis buffer (100 mM Tris-HCl (pH 7.5, manufactured by Sigma-Aldrich Co. LLC.), 2% SDS (manufactured by Sigma-Aldrich Co. LLC.), 1 mM DTT (manufactured by Sigma-Aldrich Co. LLC.), and a protease inhibitor cocktail (manufactured by Calbiochem, diluted to 1:200)) were added thereto and homogenized using a plastic homogenizer (product name: BioMasher II, manufactured by Nippi, Incorporated). The protein lysate obtained was incubated at 4° C. for 30 minutes with rotation and then boiled at 100° C. for 15 minutes. Then, centrifugation (16,000× g, 10 minutes, 4° C.) was performed, and an equal amount of a sample buffer (125 mM Tris-HCl (pH 6.8, manufactured by Sigma-Aldrich Co. LLC.), 4% SDS (manufactured by Sigma-Aldrich Co. LLC.), 20% glycerol (manufactured by FUJIFILM Wako Pure Chemical Corporation), 12% mercapto ethanol (manufactured by FUJIFILM Wako Pure Chemical Corporation), and 0.05% BPB (manufactured by NACALAI TESQUE, INC.)) was added to the resultant supernatant for dilution.

The sample prepared as above was fractionated by SDS-PAGE and transcribed into an Immobilon (R)-P polyvinylidene fluoride membrane (manufactured by EMD Millipore Corporation) by the semi-dry method, followed by blocking treatment with TBST containing 2% BSA (manufactured by NACALAI TESQUE, INC.) or 5% milk (10 mM Tris-HCl, pH 8.0, 150 mM NaCl, 0.05% Tween-20). Then, a rabbit anti-phosphorylated MARCKS antibody (1:100,000, manufactured by GE Healthcare) and a mouse anti-actin antibody (1:1000, manufactured by Santa Cruz Biotechnology, Inc.) were each diluted using TBST containing 0.2% BSA or an immunoreaction enhancer solution, to prepare a primary antibody solution. Further, an HRP-labeled anti-rabbit IgG antibody (1:3000, manufactured by GE Healthcare) and an HRP-labeled anti-mouse IgG antibody (1:3000, manufactured by GE Healthcare) were each diluted using TBST containing 0.2% BSA or an immunoreaction enhancer solution, to prepare a secondary antibody solution. The aforementioned membrane was incubated together with the primary antibody solution at 4° C. overnight, washed, and then incubated together with the secondary antibody solution at room temperature for 1 hour. The membrane after incubation was washed, and an ECL Prime Western blot detection reagent and a lumino image analyzer were used to detect a signal in each lane.

Figure 6:
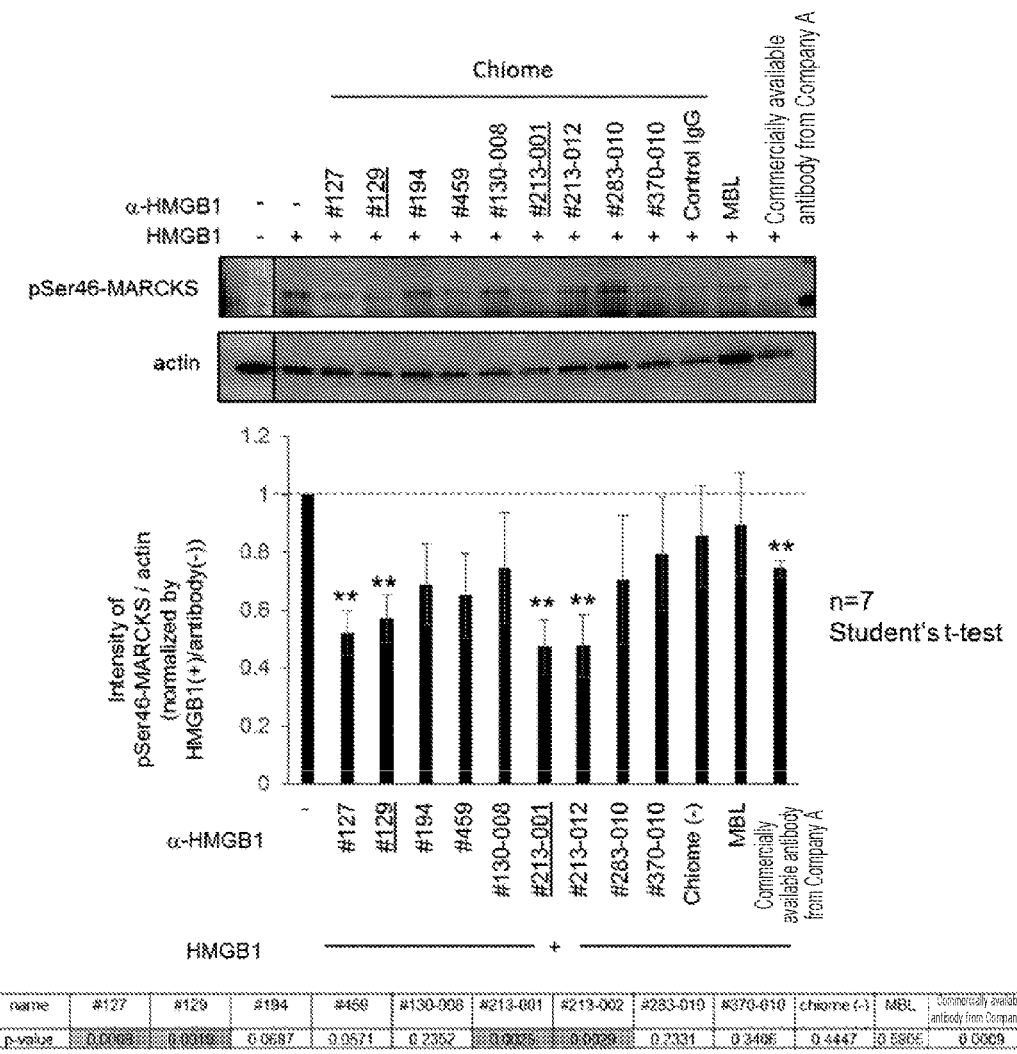
FIG. 6 shows the examination results of the human MARCKS phosphorylation inhibitory activity of the human monoclonal antibody of the present invention. The images in the upper part of the figure show the results of detecting MARCKS phosphate and actin by Western blotting. The graph in the lower part of the figure shows the results of quantifying the amount of MARCKS phosphate based on the aforementioned results by Western blotting. In the figure, "α-HMGB1" represents each antibody, "HMGB1" represents human HMGB1 protein, and "pSer46-MARCKS" represents phosphorylated MARCKS protein. Further, the vertical axis of the graph indicates the amount of phosphorylated MARCKS protein corrected based on the amount of actin (internal standard), and the horizontal axis of the graph indicates each antibody. In the graph, "**" indicates that the amount of MARKCS phosphate is significantly lower (p<0.01) than that in the antibody-free area (column "α-HMGB1 (−)/HMGB1 (+)" at the left end). From this experiment, it was revealed that monoclonal antibodies #127, #129, #213-001, and #213-012 inhibit MARCKS phosphorylation by HMGB1. The "commercially available antibody from Company A" is a commercially available anti-human HMGB1 antibody and was used as a positive control. Further, "MBL" is 2C8C antibody (anti-HMGB1 mouse antibody) of International Publication No. WO 2018/030405 (Patent Document 3), which is a prior patent application by the inventors.

The results (image) of Western blotting are shown in the upper part of FIG. 6, and the results (graph) of the amount of phosphorylated human MARCKS protein in each lane corrected using the amount of actin (internal standard) are shown in the lower part of FIG. 6. It was revealed that the amount of phosphorylated human MARCKS protein significantly decreased in the cell groups with monoclonal antibodies #127, #129, #213-001, and #213-012 added, as compared with groups with no antibody added (column represented by "−" at the left end of the graph). Further, it was revealed that the MARCKS phosphorylation inhibitory activities of these monoclonal antibodies tended to be high as compared with that of the commercially available antibody (column represented by "commercially available antibody from Company A" at the right end of the graph). The above results demonstrated that monoclonal antibodies #127, #129, #213-001, and #213-012 each had an inhibitory (suppressive) activity on phosphorylation of human MARCKS protein by human HMGB1. Accordingly, in consideration of these experimental results together with the results of Non Patent Documents 1 and 2 and Patent Document 1, these antibodies can be used as a therapeutic agent or a prophylactic agent for Alzheimer's disease.

Example 5

Amino Acid Sequences of Monoclonal Antibodies

DNA was extracted from each of the antibody-producing cells (cells that produce monoclonal antibodies #127, #129, #213-001, and #213-012) produced in Example 1, to analyze DNA sequences encoding antibody heavy- and light-chain variable regions. Further, the amino acid sequences of a heavy chain and a light chain of each monoclonal antibody were identified based on such DNA sequences. The amino acid sequences of monoclonal antibodies #127, #129, #213-001, and #213-012 were as described below. Further, FIG. 9 shows the alignment of the amino acid sequences of the heavy-chain variable regions of monoclonal antibodies #127, #129, #213-001, and #213-012 that were the human monoclonal antibodies of the present invention (the amino acid sequences of SEQ ID NOs: 2, 12, 22, and 32, respectively), and FIG. 10 shows the alignment of the amino acid sequences of the light-chain variable regions thereof (the amino acid sequences of SEQ ID NOs: 7, 17, 27 and 37, respectively). As seen from FIG. 9, amino acid residues 1 to 4, 7 to 8, 14 to 15, 17, 21 to 22, 24 to 26, 28 to 30, 31 to 33, 35 to 42, 44 to 47, 51, 56, 60 to 61, 66 to 67, 69 to 70, 73, 75, 78, 80, 85 to 87, 89 to 96, 102, 104 to 108, and 110 to 114 in the amino acid sequence of SEQ ID NO: 22 (the amino acid sequence of the heavy-chain variable region of antibody #213-001) are common to those in the amino acid sequences of the heavy-chain variable regions of monoclonal antibodies #127, #129, #213-001, and #213-012, for example. Further, as seen from FIG. 10, amino acid residues 1 to 14, 16 to 27, 32 to 49, 51 to 52, 54, 57 to 75, 77 to 88, 90, 92 to 93, 95, 97 to 102, and 104 to 107 in the amino acid sequence of SEQ ID NO: 27 (the amino acid sequence of the light-chain variable region of antibody #213-001) are common to those in the amino acid sequences of the light-chain variable regions of monoclonal antibodies #127, #129, #213-001, and #213-012, for example.

<Monoclonal Antibody #127>

```
Heavy chain of #127 (heavy-chain variable region and heavy-chain
constant region):
                                                    (SEQ ID No. 1)
EVQLLESGGGLVQPGGSLRLSCAASGFTFSSYAMSWVRQAPGKGLEWVSAISGSGGSTYYADSV

KGRFTISRDNSKNTLYLQMNSLRAEDTAVYYCTKDGYSSSWDYYYYYYGMDVWGQGTTVTVSSA

STKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFSCSVMHEALHNHYTQ

KSLSLSPGK

Heavy-chain variable region of #127:
                                                    (SEQ ID No. 2)
EVQLLESGGGLVQPGGSLRLSCAASGFTFSSYAMSWVRQAPGKGLEWVSAISGSGGSTYYADSV

KGRFTISRDNSKNTLYLQMNSLRAEDTAVYYCTKDGYSSSWDYYYYYYGMDVWGQGTTVTVSS

Heavy-chain CDR1 of #127:
                                                    (SEQ ID No. 3)
SYAMS Heavy-chain CDR2 of #127:
                                                    (SEQ ID No. 4)
AISGSGGSTYYADSVKG Heavy-chain CDR3 of #127:
                                                    (SEQ ID No. 5)
DGYSSSWDYYYYYYGMDV Light chain of #127 (light-chain variable region and light-chain
constant region):
                                                    (SEQ ID No. 6)
DIQMTQSPSSLSASVGDRVTITCRASQSVSSYLAWYQQKPGKAPKLLIYEASNLQAGVPSRFSG

SGSGTDFTLTINSLQPEDFATYYCLQHNSNPLTFGQGTKLEIKTVAAPSVFIFPPSDEQLKSGT

ASVVCLLNNFYPREAKVQWKVDNALQSGNSQESVTEQDSKDSTYSLSSTLTLSKADYEKHKVYA

CEVTHQGLSSPVTKSFNRGEC

Light-chain variable region of #127:
                                                    (SEQ ID No. 7)
DIQMTQSPSSLSASVGDRVTITCRASQSVSSYLAWYQQKPGKAPKLLIYEASNLQAGVPSRFSG

SGSGTDFTLTINSLQPEDFATYYCLQHNSNPLTFGQGTKLEIK

Light-chain CDR1 of #127:
                                                    (SEQ ID No. 8)
RASQSVSSYLA Light-chain CDR2 of #127:
                                                    (SEQ ID No. 9)
EASNLQA Light-chain CDR3 of #127:
                                                    (SEQ ID No. 10)
LQHNSNPLT <Monoclonal antibody #129>
Heavy chain of #129 (heavy-chain variable region and heavy-chain
constant region):
                                                    (SEQ ID No. 11)
EVQLLESGGGLVQPGGSLRLSCAASGFTFSSYAMSWVRQAPGKGLEWVSDISGSGGSTYYADSV

KGRFTISRDNSKNTLYLQMNSLRAEDTAVYYCARGYGMDVWGQGTMVTVSSASTKGPSVFPLAP

SSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWLNGKEYKCK
```

-continued

VSNKALPAPIEKTISKAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNHYTQKSLSLSPGK

Heavy-chain variable region of #129:
(SEQ ID No. 12)
EVQLLESGGGLVQPGGSLRLSCAASGFTFSSYAMSWVRQAPGKGLEWVSDISGSGGSTYYADSV

KGRFTISRDNSKNTLYLQMNSLRAEDTAVYYCARGYGMDVWGQGTMVTVSS

Heavy-chain CDR1 of #129:
(SEQ ID No. 13)
SYAMS

Heavy-chain CDR2 of #129:
(SEQ ID No. 14)
DISGSGGSTYYADSVKG

Heavy-chain CDR3 of #129:
(SEQ ID No. 15)
GYGMDV

Light chain of #129 (light-chain variable region and light-chain constant region):
(SEQ ID No. 16)
DIQMTQSPSSLSASVGDRVTITCRASQSVTNYLAWYQQKPGKAPKLLIYGASILETGVPSRFSG

SGSGTDFTLTINSLQPEDFATYYCLQHNSTPLTFGQGTKLEIKTVAAPSVFIFPPSDEQLKSGT

ASVVCLLNNFYPREAKVQWKVDNALQSGNSQESVTEQDSKDSTYSLSSTLTLSKADYEKHKVYA

CEVTHQGLSSPVTKSFNRGEC

Light-chain variable region of #129:
(SEQ ID No. 17)
DIQMTQSPSSLSASVGDRVTITCRASQSVTNYLAWYQQKPGKAPKLLIYGASILETGVPSRFSG

SGSGTDFTLTINSLQPEDFATYYCLQHNSTPLTFGQGTKLEIK

Light-chain CDR1 of #129:
(SEQ ID No. 18)
RASQSVTNYLA

Light-chain CDR2 of #129:
(SEQ ID No. 19)
GASILET

Light-chain CDR3 of #129:
(SEQ ID No. 20)
LQHNSTPLT

<Monoclonal antibody #213-001>
Heavy chain of #213-001 (heavy-chain variable region and heavy-chain constant region):
(SEQ ID No. 21)
EVQLVQSGAEVKKPGSSVKVSCKASGGTFSSYAISWVRQAPGQGLEWMGGIIPIFGRANYAQKF

QGRVTITADESTSTAYMELSSLRSEDTAVYYCASLVTDYWGQGTLVTVSSASTKGPSVFPLAPS

SKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQKSLSLSPGK

Heavy-chain variable region of #213-001:
(SEQ ID No. 22)
EVQLVQSGAEVKKPGSSVKVSCKASGGTFSSYAISWVRQAPGQGLEWMGGIIPIFGRANYAQKF

QGRVTITADESTSTAYMELSSLRSEDTAVYYCASLVTDYWGQGTLVTVSS

Heavy-chain CDR1 of #213-001:
(SEQ ID No. 23)
SYAIS

-continued

Heavy-chain CDR2 of #213-001:
(SEQ ID No. 24)
GIIPIFGRANYAQKFQG

Heavy-chain CDR3 of #213-001:
(SEQ ID No. 25)
LVTDY

Light chain of #213-001 (light-chain variable region and light-chain constant region):
(SEQ ID No. 26)
DIQMTQSPSSLSASTGDRVTITCRASQGISSYLAWYQQKPGKAPKLLIYAASTLQSGVPSRFSG

SGSGTDFTLTISSLQPEDFATYYCQQANSFPITFGQGTRLEIKTVAAPSVFIFPPSDEQLKSGT

ASVVCLLNNFYPREAKVQWKVDNALQSGNSQESVTEQDSKDSTYSLSSTLTLSKADYEKHKVYA

CEVTHQGLSSPVTKSFNRGEC

Light-chain variable region of #213-001:
(SEQ ID No. 27)
DIQMTQSPSSLSASTGDRVTITCRASQGISSYLAWYQQKPGKAPKLLIYAASTLQSGVPSRFSG

SGSGTDFTLTISSLQPEDFATYYCQQANSFPITFGQGTRLEIK

Light-chain CDR1 of #213-001:
(SEQ ID No. 28)
RASQGISSYLA

Light-chain CDR2 of #213-001:
(SEQ ID No. 29)
AASTLQS

Light-chain CDR3 of #213-001:
(SEQ ID No. 30)
QQANSFPIT

<Monoclonal antibody #213-012>
Heavy chain of #213-012 (heavy-chain variable region and heavy-chain constant region):
(SEQ ID No. 31)
EVQLVQSGAEVKKPGSSVKVSCKASGGTFSSYAISWVRQAPGQGLEWMGGIIPIFGTANYAQKF

QGRVTITADESTSTAYMELSSLRSEDTAVYYCASLVTDYWGQGTLVTVSSASTKGPSVFPLAPS

SKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQKSLSLSPGK

Heavy-chain variable region of #213-012:
(SEQ ID No. 32)
EVQLVQSGAEVKKPGSSVKVSCKASGGTFSSYAISWVRQAPGQGLEWMGGIIPIFGTANYAQKF

QGRVTITADESTSTAYMELSSLRSEDTAVYYCASLVTDYWGQGTLVTVSS

Heavy-chain CDR1 of #213-012:
(SEQ ID No. 33)
SYAIS

Heavy-chain CDR2 of #213-012:
(SEQ ID No. 34)
GIIPIFGTANYAQKFQG

Heavy-chain CDR3 of #213-012:
(SEQ ID No. 35)
LVTDY

Light chain of #213-012 (light-chain variable region and light-chain constant region):
(SEQ ID No. 36)
DIQMTQSPSSLSASTGDRVTITCRASQGISSYLAWYQQKPGKAPKLLIYAASTLQSGVPSRFSG

SGSGTDFTLTISSLQPEDFATYYCQQANSFPITFGQGTRLEIKTVAAPSVFIFPPSDEQLKSGT

```
                              -continued
ASVVCLLNNFYPREAKVQWKVDNALQSGNSQESVTEQDSKDSTYSLSSTLTLSKADYEKHKVYA

CEVTHQGLSSPVTKSFNRGEC

Light-chain variable region of #213-012:
                                                      (SEQ ID No. 37)
DIQMTQSPSSLSASTGDRVTITCRASQGISSYLAWYQQKPGKAPKLLIYAASTLQSGVPSRFSG

SGSGTDFTLTISSLQPEDFATYYCQQANSFPITFGQGTRLEIK

Light-chain CDR1 of #213-012:
                                                      (SEQ ID No. 38)
RASQGISSYLA Light-chain CDR2 of #213-012:
                                                      (SEQ ID No. 39)
AASTLQS Light-chain CDR3 of #213-012:
                                                      (SEQ ID No. 40)
QQANSFPIT <Heavy-chain constant region of human monoclonal antibody
of present invention>
                                                      (SEQ ID No. 41)
ASTKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFSCSVMHEALHNHYT

QKSLSLSPGK

<Light-chain constant region (κ chain) of human monoclonal
antibody of present invention>
                                                      (SEQ ID No. 42)
TVAAPSVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC
```

Example 6

Subcutaneous Administration of Monoclonal Antibody #129

Monoclonal antibody #129 was subcutaneously administered to Alzheimer's disease model mice, to examine the effects on cognitive impairment. As the Alzheimer's disease model mice, 5xFAD transgenic mice purchased from the Jackson Laboratory (USA) (which will be hereinafter referred to as "5xFAD mice"; Oakley et al., J Neurosci 26, 10129-10140 (2006)) were used. The 5xFAD mice were Alzheimer's disease model mice over-expressing mutant human APP (770) including Swedish-type (KM670/671NL), Florida-type (I716V), and London-type (V717I) familial Alzheimer's disease (FAD) mutations and human PS1 including two FAD mutations. Further, the background of such mice is C57BL/SJL strain obtained by mating C57BL/6J female mice and SJL/J male mice. Therefore, the 5xFAD mice and sibling B6/SJL non-transgenic mice as control mice (normal mice) were used in the following experiments.

Along the schedule shown in FIG. 11A, monoclonal antibody #129 or control human IgG (IgG1κ chain) was subcutaneously administered to the normal mice and 6-month-old 5xFAD mice immediately after the onset. The single dose of each antibody was 1 µg/Kg body weight or 10 µg/Kg body weight, and the antibody was administered 9 times in total over 8 weeks. The cognitive function and dendritic spine density at 8 months of age were examined for each of the four groups of mice treated in this way.

FIG. 11B shows the results for the cognitive function. The four bar graphs in FIG. 11B represent the results for "B6/SJL+ctrl IgG", "B6/SJL+α-HMGB1", "5xFAD+ctrl IgG", and "5xFAD+α-HMGB1", respectively from the left. As a result of examining the cognitive function by the Y-maze test, a significant decrease in cognitive function was observed in the 5xFAD mice to which control human IgG was administered, as compared with that in the normal mice, and it turned out that cognitive dysfunction progressed in the 8-month-old 5xFAD mice. Meanwhile, no significant difference in cognitive function was observed in the 5xFAD mice to which monoclonal antibody #129 was administered, as compared with that in the normal mice. Further, it turned out that the cognitive function was significantly improved in the 5xFAD mice to which monoclonal antibody #129 was administered, as compared with that in the 5xFAD mice to which control human IgG was administered.

Further, FIG. 11E shows the results for the dendritic spine density. The bar graphs in FIG. 11E represent the results for "B6/SJL+ctrl IgG", "B6/SJL+α-HMGB1", "5xFAD+ctrl IgG", and "5xFAD+α-HMGB1", respectively from the left.

As a result of examining the dendritic spine density one layer of the parietal cortex (retrosplenial granular cortex) in the aforementioned mice using a two-photon excitation microscope, a significant decrease in the number of dendritic spines was observed in the 5xFAD mice to which control human IgG was administered, as compared with that in the normal mice. Meanwhile, no significant difference in the number of dendritic spines was observed in the 5xFAD mice to which monoclonal antibody #129 was administered, as compared with that in the normal mice. Further, it turned out that a significant increase in the number of dendritic spines was observed in the 5xFAD mice to which monoclonal antibody #129 was administered, as compared with that in the 5xFAD mice to which control human IgG was administered.

These results demonstrated that subcutaneous administration of monoclonal antibody #129 exerted the effects of suppressing the progression of cognitive dysfunction in Alzheimer's disease model mice and suppressing the decrease in dendritic spine density to improve them to the same level as in the normal mice.

Example 7

Figure 12A:
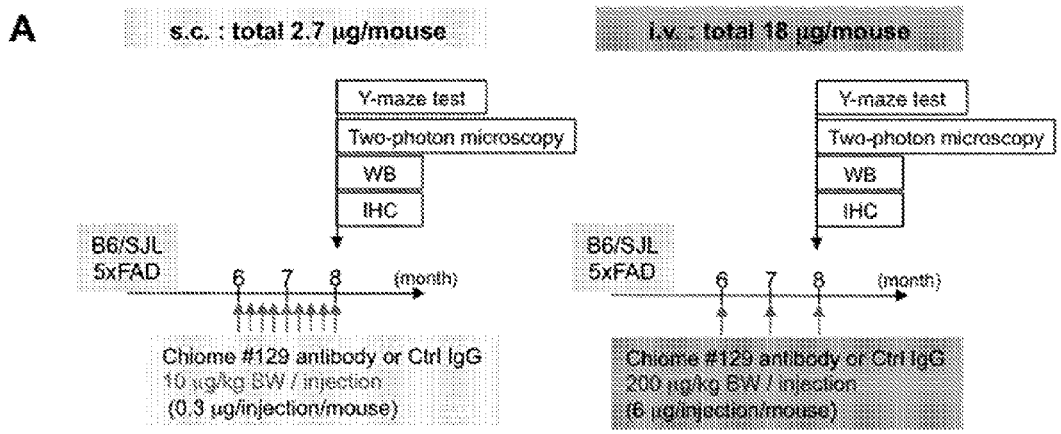
FIG. 12A shows the outline of the schedule of antibody administration to mice.

Comparison of Therapeutic Effects of Monoclonal Antibody #129 Via Different Route of Administration Then, monoclonal antibody #129 was injected subcutaneously (s.c.) or intravenously (i.v.) to the 5xFAD mice, to compare the difference in effects depending on the administration route. Monoclonal antibody #129 and control human IgG were subcutaneously administered or intravenously injected to 6-month-old 5xFAD mice immediately after the onset and the normal mice over 8 weeks. FIG. 12A shows the outline of administration schedule. In the case of subcutaneous administration, 10 µg/Kg body weight of the antibody was administered to the mice 9 times in total (total dose per mouse was 2.7 µg). Further, in the case of intravenous injection, 200 µ/Kg body weight of the antibody was administered to the mice 3 times in total (total dose per mouse was 18 µg). The cognitive function and dendritic spine density at 8 months of age were examined for each mice treated in this way. FIG. 12A shows the schedule of such administration experiment.

Figure 12B:
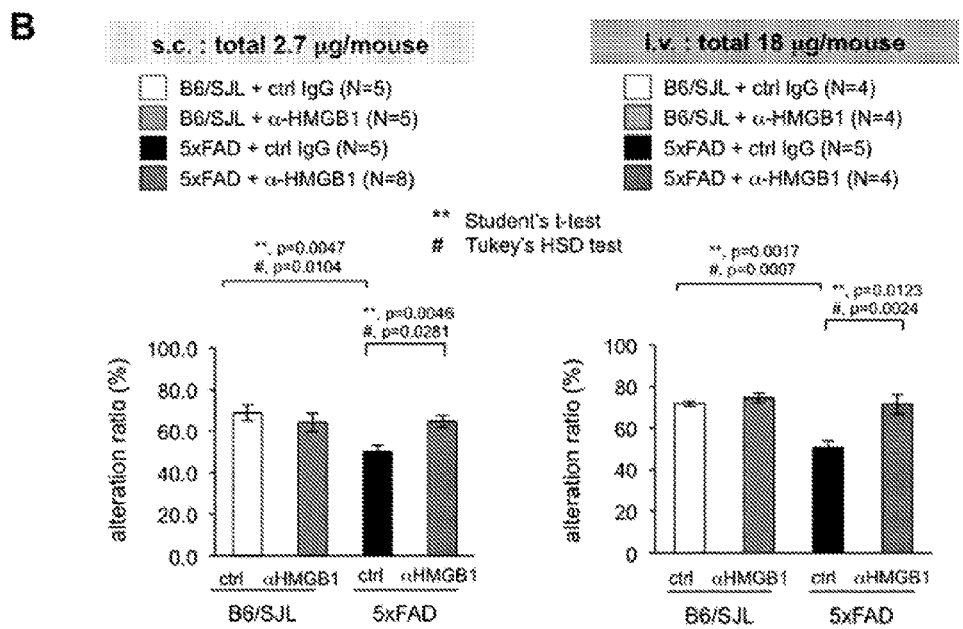
FIG. 12B shows the results of quantifying the cognitive function in each administration group by the Y-maze test. In the figure, "s.c." represents subcutaneous injection, and "i.v." represents intravenous injection. In the figure, "B6/SJL" represents B6/SJL non-transgenic mice (normal mice), and "5xFAD" represents 5xFAD transgenic mice. In the figure, "B6/SJL+ctrl IgG" represents normal mice to which control human IgG was administered, "B6/SJL+α-HMGB1" represents normal mice to which monoclonal antibody #129 was administered, "5xFAD+ctrl IgG" represents Alzheimer's disease model mice to which control human IgG was administered, and "5xFAD+α-HMGB1" represents Alzheimer's disease model mice to which monoclonal antibody #129 was administered. In both graphs on the left and right of FIG. 12B, the bar graphs show the results of "B6/SJL+ctrl IgG", "B6/SJL+α-HMGB1", "5xFAD+ctrl IgG", and "5xFAD+α-HMGB1", respectively from the left.

As shown in the left graph of FIG. 12B, the results consistent with Example 6 were obtained in the subcutaneous injection group, as a result of examining the cognitive function of the aforementioned mice by the Y-maze test. As shown in the right graph of FIG. 12B, the same results as in the subcutaneous administration group were obtained also in the intravenous injection group. That is, in any route of subcutaneous administration and intravenous injection, a significant decrease in cognitive function was observed in the 5xFAD mice to which control human IgG was administered, as compared with that in the normal mice, whereas no significant difference in cognitive function was observed in the 5xFAD mice to which monoclonal antibody #129 was administered, as compared with that in the normal mice. Further, it turned out that the cognitive function was significantly improved in the 5xFAD mice to which monoclonal antibody #129 was administered, as compared with that in the 5xFAD mice to which control human IgG was administered. Likewise, it turned out that subcutaneous administration and intravenous injection of monoclonal antibody #129 exhibited a similar action of suppressing the decrease in dendritic spine density in the 5xFAD mice (no data shown).

Example 8

Translocation of Monoclonal Antibody #129 to Brain Tissue

Figure 13:
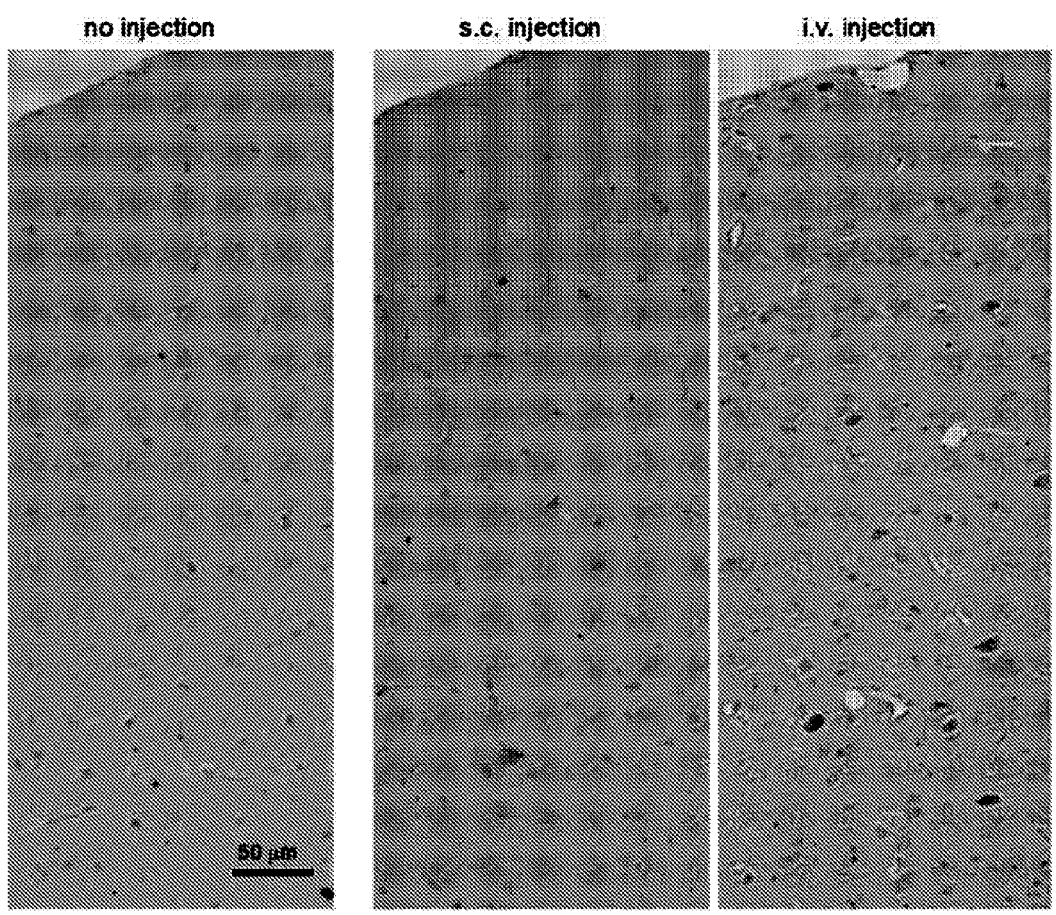
FIG. 13 shows localization of monoclonal antibody #129 in the mouse brain tissue to which monoclonal antibody #129 was subcutaneously administered (s.c. injection) or intravenously injected (i.v. injection). In the figure, "no injection" indicates a result of staining a normal mouse brain with no antibody administered.

Monoclonal antibody #129 was administered to the normal mice over 8 weeks on the same schedule as in Example 7, and transfer of monoclonal antibody #129 to the mouse brain tissue was confirmed. Specifically, the brain tissue was collected from mice to which monoclonal antibody #129 was subcutaneously administered or intravenously injected and subjected to biotin-avidin system immunohistochemical staining using a biotin-labeled anti-human IgG antibody. As seen from the results shown in FIG. 13, a staining signal of monoclonal antibody #129 in the brain tissue was obtained in both mice with subcutaneous administration (s.c. injection) and intravenous injection (i.v. injection). These results showed that monoclonal antibody #129 subcutaneously administered and intravenously injected was transferred into the mouse brain.

Example 9

Examination of Side Effects of Monoclonal Antibody #129

Further, the inventors administered control human IgG or monoclonal antibody #129 to the normal mice over 8 weeks on the same schedule as in Example 7, to examine whether or not monoclonal antibody #129 caused undesired side effects. As a result of comparing the appearance of 8-month-old mice to which control human IgG or monoclonal antibody #129 was administered, no abnormality was observed in the body shape and epidermis in any of the groups. As a result of comparing the changes in body weight from 6-month-old (24 week-old) mice to 8-month-old (32 week-old) mice in each of the subcutaneous administration and intravenous injection groups, no difference was observed between monoclonal antibody #129 and control human IgG.

Further, the liver, lung, kidney, spleen, heart, intestine, muscle, and skin tissue were collected from the aforementioned 8-month-old mice and subjected pathological inspection. As a result, no abnormal findings due to administration of monoclonal antibody #129 were observed in any of the tissues as compared with that of control human IgG. Further, no morphological difference due to administration of monoclonal antibody #129 was observed as compared with that of the normal mice to which no antibody was administered. From the above, it was shown that monoclonal antibody #129 can improve the cognitive dysfunction in Alzheimer's disease model mice without any significant side effects.

INDUSTRIAL APPLICABILITY

The present invention can provide a human monoclonal antibody that has a high inhibitory activity on phosphorylation of Ser46 of human MARCKS and binds specifically to human HMGB1, and a pharmaceutical composition or the like containing the antibody as an active component for treating or preventing Alzheimer's disease.

The invention claimed is:

1. A human monoclonal antibody that specifically binds to human High Mobility Group Box 1 (HMGB1), wherein the human monoclonal antibody comprises:
   a heavy-chain complementarity determining region (CDR) 1 consisting of the amino acid sequence set forth in SEQ ID NO:13, a heavy-chain CDR2 consisting of the amino acid sequence set forth in SEQ ID NO:14, and a heavy-chain CDR3 consisting of the amino acid sequence set forth in SEQ ID NO:15; and
   a light-chain CDR1 consisting of the amino acid sequence set forth in SEQ ID NO: 18, a light-chain CDR2 consisting of the amino acid sequence set forth in SEQ ID NO: 19, and a light-chain CDR3 consisting of the amino acid sequence set forth in SEQ ID NO: 20.

2. The human monoclonal antibody according to claim 1, wherein the human monoclonal antibody comprises a heavy-chain variable region consisting of an amino acid sequence having a sequence identity of at least 80% with the amino acid sequence set forth in SEQ ID NO: 12 and a light-chain variable region consisting of an amino acid sequence having a sequence identity of at least 80% with the amino acid sequence set forth in SEQ ID NO:17.

3. The human monoclonal antibody according to claim 2, wherein the human monoclonal antibody comprises a heavy-chain consisting of an amino acid sequence having a sequence identity of at least 80% with the amino acid sequence set forth in SEQ ID NO:11 and a light-chain consisting of an amino acid sequence having a sequence identity of at least 80% with the amino acid sequence set forth in SEQ ID NO: 16.

4. A composition comprising the human monoclonal antibody according to claim 1.

5. A composition comprising the human monoclonal antibody according to claim 2.

6. A composition comprising the human monoclonal antibody according to claim 3.

7. A method for treating Alzheimer's disease, comprising a step of administering the human monoclonal antibody according to claim 1 to a subject in need of the treatment of Alzheimer's disease.

* * * * *